United States Patent
Ochiya et al.

(10) Patent No.: US 7,332,336 B2
(45) Date of Patent: Feb. 19, 2008

(54) METHODS FOR INDUCING DIFFERENTIATION OF PLURIPOTENT CELLS

(75) Inventors: Takahiro Ochiya, Chuo-ku (JP); Takumi Teratani, Matsudo (JP)

(73) Assignee: Effector Cell Institute, Inc., Meguro-Ku (JP)

( * ) Notice: Subject to any disclaimer, the term of this patent is extended or adjusted under 35 U.S.C. 154(b) by 471 days.

(21) Appl. No.: 10/789,159

(22) Filed: Feb. 27, 2004

(65) Prior Publication Data
US 2005/0042748 A1 Feb. 24, 2005

(30) Foreign Application Priority Data
Aug. 19, 2003 (JP) .............................. 2003-295523

(51) Int. Cl.
C12N 5/00 (2006.01)
C12N 5/08 (2006.01)
(52) U.S. Cl. ...................... 435/377; 435/325; 435/370; 435/372; 435/375
(58) Field of Classification Search ...................... None
See application file for complete search history.

(56) References Cited

U.S. PATENT DOCUMENTS

| | | | |
|---|---|---|---|
| 5,380,660 | A | 1/1995 | Jefferson et al. |
| 6,458,589 | B1 | 10/2002 | Rambhatla et al. |
| 6,506,574 | B1 | 1/2003 | Rambhatla et al. |
| 2001/0049139 | A1 | 12/2001 | Lagasse et al. |
| 2002/0142457 | A1 | 10/2002 | Umezawa et al. |
| 2002/0160511 | A1 | 10/2002 | Rambhatla et al. |
| 2002/0164307 | A1 | 11/2002 | Habener et al. |
| 2003/0003573 | A1 | 1/2003 | Rambhatle et al. |
| 2003/0031657 | A1 | 2/2003 | Habener et al. |
| 2003/0032182 | A1 | 2/2003 | Kubota et al. |
| 2003/0048931 | A1 | 3/2003 | Johnson et al. |
| 2003/0082155 | A1 | 5/2003 | Habener et al. |
| 2003/0186439 | A1 | 10/2003 | Nakauchi et al. |
| 2004/0029153 | A1 | 2/2004 | Takahashi et al. |
| 2004/0152095 | A1 | 8/2004 | Tanimizu et al. |
| 2004/0191902 | A1 | 9/2004 | Hambour et al. |
| 2005/0003456 | A1 | 1/2005 | Miyoshi et al. |
| 2005/0037493 | A1 | 2/2005 | Mandalam et al. |
| 2005/0233449 | A1 | 10/2005 | Lee et al. |

FOREIGN PATENT DOCUMENTS

| | | |
|---|---|---|
| HU | 9902752 | 12/1999 |
| JP | 9-103291 | 4/1997 |
| JP | 2000-287680 A | 10/2000 |
| JP | 2001-316285 A | 11/2001 |
| JP | 2002-78482 | 3/2002 |
| WO | WO 00/50048 A2 | 8/2000 |
| WO | WO 01/39784 A1 | 6/2001 |
| WO | WO 02/29012 A1 | 4/2002 |
| WO | WO 02/062969 A2 | 8/2002 |
| WO | WO 02/074937 A1 | 9/2002 |
| WO | WO 02/096203 A1 | 12/2002 |
| WO | WO 2004/007683 A2 | 1/2004 |
| WO | WO 2004/087896 A2 | 10/2004 |

OTHER PUBLICATIONS

Castro RF et al. 2002. Failure of bone marrow cells to transdifferentiate into neural cells in vivo. Science 297: 1299.*
Mezey E et al. and Castro RF et al. 2003. "Comment on Failure of bone marrow cells to transdifferentiate into neural cells in vivo", "Response to Comment on Failure of bone marrow cells to transdifferentiate into neural cells in vivo." Science 299:1184b,c.*
Reinecke H et al. 2002. Skeletal muscle stem cells do not transdifferentiate into cardiomyocytes after cardiac grafting. J Mol Cell Cardiol 34: 241-249.*
Murry CE et al. 2004. Hematopoietic stem cells do not transdifferentiate into cardiac mycytes in myocardial infarcts. Nature 428: 664-668.*
Azuma, H., et al., "Enrichment of Hepatic Progenitor Cells from Adult Mouse Liver," *Hepatology*, 2003, pp. 1385-1394, vol. 37(6).
Chinzei, R., et al., "Embryoid-Body Cells Derived from a Mouse Embryonic Stem Cell Line Show Differentiation Into Functional Hepatocytes," *Hepatology*, 2002, pp. 22-29, vol. 36(1).
Choi, D., et al., "In Vivo Differentiation of Mouse Embryonic Stem Cells Into Hepatocytes," *Cell Transplantation*, 2002, pp. 359-368, vol. 11(4).
Fair, JH, et al., "Induction of Hepatic Differentiation in Embryonic Stem Cells By Co-Culture With Embryonic Cardiac Mesoderm," *Surgery*, 2003, pp. 189-196, vol. 134(2).
Hamazaki, T., et al., "Hepatic Maturation in Differentiating Embryonic Stem Cells In Vitro," *FEBS Letters*, 2001, pp. 15-19, vol. 497(1).
He ZP, et al., "Differentiation of Putative Hepatic Stem Cells Derived from Adult Rats into Mature Hepatocytes in the Presence of Epidermal Growth Factor and Hepatocyte Growth Factor," *Differentiation*, 2003, pp. 281-290, vol. 71(4-5).
Hu, A., et al., "Hepatic Differentiation from Embryonic Stem Cells In Vitro," *Chinese Medical Journal*, 2003, pp. 1893-1897, vol. 116(12).
Ishizaka, S., et al., "Development of Hepatocytes from ES Cells After Transfection with the HNF-3β Gene," *FASEB Journal*, 2002, pp. 1444-1446, vol. 16(11).
Itskovitz-Eldor, J., et al, "Differentiation of Human Embryonic Stem Cells Into Embryoid Bodies Comprising the Three Embryonic Germ Layers," *Molecular Medicine*, 2000, pp. 88-95, vol. 6(2).
Jochheim, A., et al, "Quantitative Gene Expression Profiling Reveals a Fetal Hepatic Phenotype of Murine ES-Derived Hepatocytes," *Int. J. Dev. Biol.*, 2004, pp. 23-29, vol. 48(1).
Jones, E.A., et al., "Hepatic Differentiation of Murine Embryonic Stem Cells," *Experimental Cell Research*, 2002, pp. 15-22, vol. 272(1).

(Continued)

*Primary Examiner*—Sandra Saucier
*Assistant Examiner*—Lora E Barnhart
(74) *Attorney, Agent, or Firm*—Townsend and Townsend and Crew LLP

(57) ABSTRACT

The present invention provides methods for inducing the differentiation of pluripotent cells. The present inventors succeeded in differentiating hepatocytes from ES cells without EB formation, using simple adherent monoculturing in media comprising several growth factors in culture dishes with two different matrices.

8 Claims, 19 Drawing Sheets

OTHER PUBLICATIONS

Kanda, S., et al., "In Vitro Differentiation of Hepatocyte-Like Cells from Embryonic Stem Cells Promoted By Gene Transfer of Hepatocyte Nuclear Factor 3 β," *Hepatology Research*, 2002, pp. 225-231, vol. 26(3).

Kuai, XL, et al., "Generation of Hepatocytes From Cultured Mouse Embryonic Stem Cells," *Liver Transplantation*, 2003, pp. 1094-1099, vol. 9(10).

Mitaka, T. et al., "Effects of Mitogens and Co-Mitogens on the Formation of Small-Cell Colonies in Primary Cultures of Rat Hepatocytes," *Journal of Cellular Physiology*, 1993, pp. 461-468, vol. 157(3).

Miyashita, H., et al., "Evidence for Hepatocyte Differentiation from Embryonic Stem Cells in Vitro," *Cell Transplantation*, 2002, pp. 429-434, vol. 11(5).

Ochiya, T., et al., "Hepatic Cell Differentiation from ES Cells and Progress Toward Liver Regenerative Medicine," *The 2nd Meeting of the Japanese Society for Regenerative Medicine*, 2003, pp. 89(1433), vol. 2(Suppl).

Ochiya, T., "Differentiation of Embryonic Stem Cells Into Hepatocytes: Biological Functions and Therapeutic Application," 2004, *Keystone Symposia*, 2004, pp. 104(337), Vol. Stem Cells.

Oh, SH, et al., "Hepatocyte Growth Factor Induces Differentiation of Adult Rat Bone Marrow Cells Into a Hepatocyte Lineage in Vitro," 2000, *Biochemical and Biophysical Research Communications*, 2000, pp. 500-504, vol. 279(2).

Okumoto, K., et al., "Differentiation of Bone Marrow Cells Into Cells That Express Liver-Specific Genes In Vitro: Implication of the Notch Signals in Differentiation," *Biochemical and Biophysical Research Communications*, 2003, pp. 691-695, vol. 304(4).

Rambhatla, L., et al., "Generation of Hepatocyte-Like Cells from Human Embryonic Stem Cells," *Cell Transplantation*, 2003, pp. 1-11, Vo. 12(1).

Ruhnke, M., et al., "Long-Term Culture and Differentiation of Rat Embryonic Stem Cell-Like Cells Into Neuronal Gilal, Endothelial, and Hepatic Lineages," *Stem Cells*, 2003, pp. 428-436, vol. 21(4).

Sachinidis, A.., et al., "Identification of Plateled-Derived Growth Factor-BB as Cardiogenesis-Inducing Factor in Mouse Embryonic Stem Cells Under Serum-Free Conditions," *Cellular Physiology and Biochemistry*, 2003, pp. 423-429, vol. 13(6).

Schuldiner, M., et al. , "Effects of Eight Growth Factors on the Differentiation of Cells Derived From Human Embryonic Stem Cells," *Proceedings of the Nat'l Academy of Sciences USA*, 2000, pp. 11307-11312, vol. 97(21).

Schwartz, R.E., et al., "Multipotent Adult Progenitor Cells From Bone Marrow Differentiate Into Functional Hepatocyte-Like Cells," *The Journal of Clinical Investigation*, 2002, pp. 1291-1302, vol. 109(10).

Suzuki, A., et al. "Development and Disease: Role for Growth Factors and Extracellular Matrix in Controlling Differentiation of Prospectively Isolated Hepatic Stem Cells," *Development* 2003, pp. 2513-2524, vol. 130(11).

Tanaka, Y. et al. "Expressions of Hepatobiliary Organic Anion Transporters and Billrubin-Conjugating Enzyme in Differentiating Embryonic Stem Cells," *Biochemical and Biophysical Research Communications*, 2003, pp. 324-330, vol. 309(2).

Teratani, T. et al. "Induction of Hepatic Cell Differentiation from *Mecaca fescicularis* ES Cells," *The 2nd Meeting of the Japanese Society for Regenerative Medicine*, 2003, pp. 92(1451), vol. 2(Suppl).

Teratani, T., et al, "Differentiation of Embryonic Stem Cells into Hepatocytes: Biological Functions and Therapeutic Application," *Dal 4 Kai Monbukagakusyou Tokutel Ryoiki Kenkyu Gan 6 Ryoiki Wakate Kenkyusya Workshop*, 2003, p. 198(065).

Teratani, T., et al., "Differentiation of Functional Hepatocytes from ES Cells in Monoculture and Therapeutic Application for Liver Cirhosis," *The 62nd Annual Meeting of the Japanese Cancer Association*, 2003, p. 3212-OP.

Teratani, T., et al., "Derivation of Hepatocytes from Stem Cells in Adherent Monoculture System," *The 26th Annual Meeting of the Molecular Biology Society of Japan*, 2003, p. O4K-10.

Yamada, T. et al., "In Vitro Differentiation of Embryonic Stem Cells into Hepatocyte-Like Cells Identified by Cellular Uptake of Indocyanine Green," Stem Cells, 2002, pp. 146-154, vol. 20(2).

Yamamoto, H. et al., "Differentiation of Embryonic Stem Cells Into Hepatocytes: Biological Functions and Therapeutic Application," *Hepatology*, 2003, pp. 983-993, vol. 37(5).

Yamamoto Y. et al., "Expression Profiles of Transcription Factors in Hepatic Commitment of ES Cells," *The 26th Annual Meeting of the Molecular Biology Society of Japan*, 2003, p. O1O-2.

Yin, Y. et al., "$AFP^+$, ESC-Derived Cells Engraft and Differentiate into Hepatocytes in Vivo," *Stem Cells*, 2002, pp. 338-346, vol. 20(4).

Yoshida, N., et al, "Induction of Donor-Specific Tolerance to Allogeneic Hepatocytes by Allogeneic Bone Marrow Transplantation," Hepatology Research, 2003, pp. 148-153, vol. 26(2).

Abe, Koichiro et al.; "Endoderm-specific gene expression in embryonic stem cells differentiated to embryoid bodies"; *Experimental Cell Research*; 1996; pp. 27-34; vol. 229; Academic Press, Inc.

Aubert, Jerôme et al.; "Functional gene screening in embryonic stem cells implicates Wnt antagonism in neural differentiation"; *Nature Biotechnology*; Dec. 2002; pp. 1240-1245; vol. 20; Nature Publishing Group.

Bain, Gerard et al.; "Embryonic stem cell express neuronal properties in Vitro"; *Developmental Biology*; 1995; pp. 342-357; vol. 168; Academic Press, Inc.

Bradley, Allan et al.; "Formation of germ-line chimaeras from embryo-derived teratocarcinoma cell lines"; *Nature*; May 17, 1984; pp. 255-256; vol. 309.

Camper, Sally A. and Shirley M. Tilghman; "The activation and silencing of gene transcription in the liver" *Biotechnology*; 1991; pp. 81-87; vol. 16.

Evans, M. J. and M. H. Kaufman; "Establishment in culture of pluripotential cells from mouse embryos" *Nature*; Jul. 9, 1981; pp. 154-156; vol. 292; Macmillan Journals Ltd.

Keller, Gordon M.; "In vitro differentiation of embryonic stem cells" *Current Opinion in Cell Biology*; 1995; pp. 862-869; vol. 7; Current Biology Ltd.

Libbrecht, Louis and Tania Roskams; "Hepatic progenitor cells in human liver diseases"; *Cell and Developmental Biology*; 2002; pp. 389-396; vol. 13; Elsevier Science Ltd.

Martin, Gail R.; "Isolation of a pluripotent cell line from early mouse embryos cultured in medium conditioned by teratocarcinoma stem cells"; *Proc. Natl. Acad. Sci. U.S.A.*; Dec. 1981; pp. 7634-7638; vol. 78, No. 12.

Medvinsky, Alexander and Austin Smith; "Fusion brings down barriers"; *Nature*; Apr. 24, 2003; pp. 823-825; vol. 422; Nature Publishing Group.

Michalopoulos, George K. and Marie C. DeFrances; "Liver Regeneration"; *Science*; Apr. 4, 1997; pp. 60-66; vol. 276.

Nahon, Jean Louis; "The regulation of albumin and α-fetoprotein gene expression in mammals"; *Biochimie*; 1987; pp. 445-459; vol. 69 ; Société de Chimie biologique/Elsevier, Paris.

Pittenger, Mark F. et al.; "Multilineage potential of adult human mesenchymal stem cells"; *Science*; Apr. 2, 1999; pp. 143-147; vol. 284.

Sánchez-Carpintero, R. and J. Narbona; "Executive system: A conceptual review and its study in children with attention-deficit hyperactivity disorder (Translation)"; *Rev. Neurol.*; 2001; pp. 47-53; vol. 33, No. 1; Revista Neurologia (with English Abstract).

Schmitt, Regina M. et al.; "Hematopoietic development of embryonic stem cells in vitro: cytokine and receptor gene expression"; *Genes and Development*; 1991; pp. 728-740; vol. 5; Cold Spring Harbor Laboratory.

Suzuki, Atsushi et al.; "Clonal identification and characterization of self-renewing pluripotent stem cells in the developing liver"; *The Journal of Cell Biology*; Jan. 7, 2002; pp. 173-184; vol. 156, No. 1; The Rockefeller University Press.

Williams, R. Lindsay et al.; "Myeloid leukaemia inhibitory factor maintains the developmental potential of embryonic stem cells;" *Nature*; Dec. 15, 1988; pp. 684-687; vol. 336.

Ochiya, et al.; U.S. Appl. No. 11/210,337; "Human hepatocyte-like cells and uses thereof;" filed on Aug. 23, 2005.

Kamiya, et al.; "Fetal Liver Development Requires a Paracrine-Action of Oncostatin M Through The gp130 Signal Transducer;" *The EMBO Journal*; 1999; pp. 2127-2136; vol. 18; No. 8; European Molecular Biology Organization.

Lee, et al.; "In Vitro Hepatic Differentiation of Human Mesenchymal Stem Cells;" *Hepatology*; Dec. 2004; pp. 1275-1284; vol. 40; No. 6.

Lee, et al.; Isolation of Multipotent Mesenchymal Stem Cells from Umbilical Cord Blood; *Blood*; Mar. 1, 2004; pp. 1669-1675; vol. 103; No. 5.

\* cited by examiner

FIG. 2
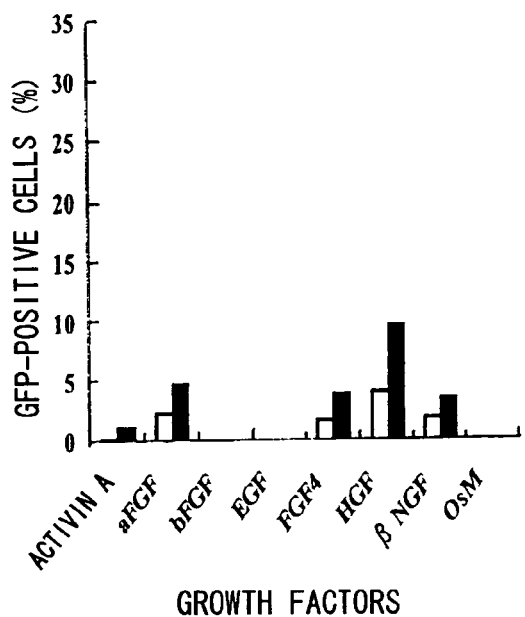
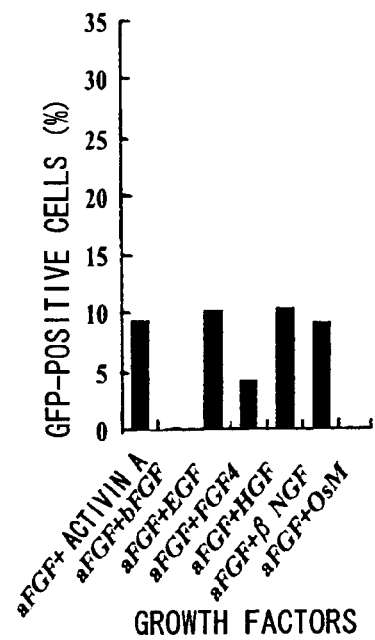
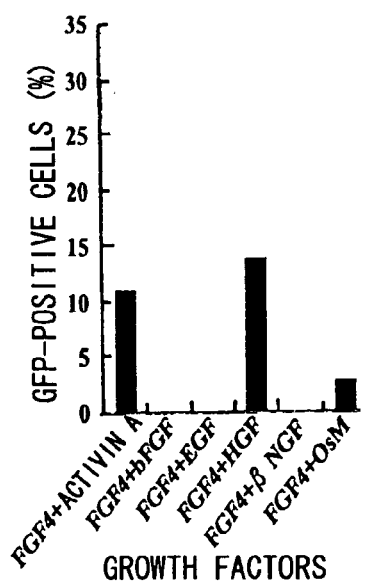
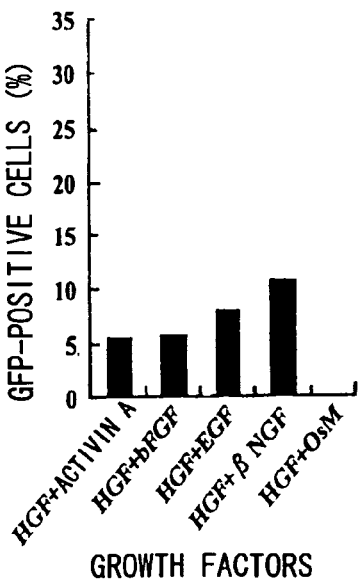
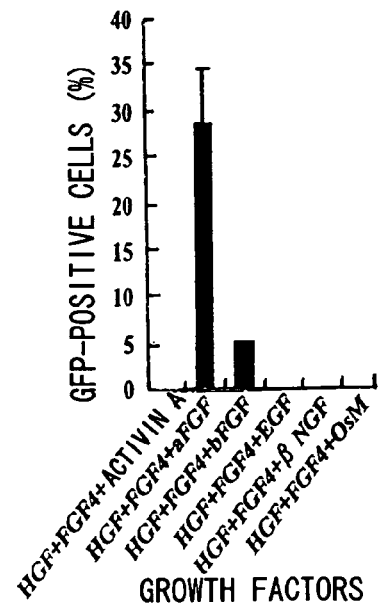

FIG. 3
A
PERCENTAGE OF GFP-POSITIVE
CELLS, 38.4%
B
C
PERCENTAGE OF GFP-POSITIVE
CELLS, 2.8%
D
PERCENTAGE OF GFP-POSITIVE
CELLS, 29.6%
E
PERCENTAGE OF GFP-POSITIVE
CELLS, 8.4%
F
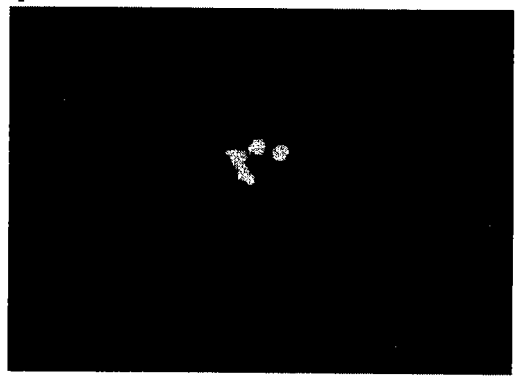
PERCENTAGE OF GFP-POSITIVE
CELLS, 1.6%

FIG. 5
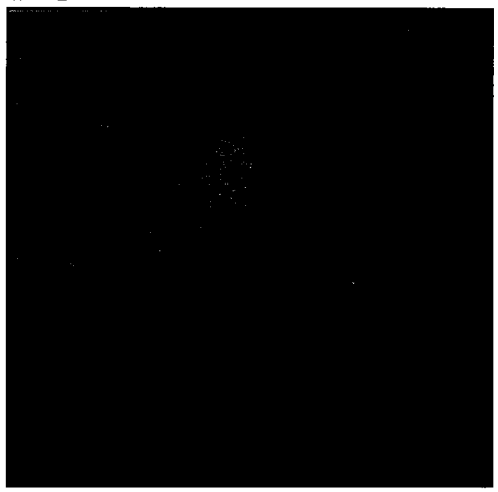
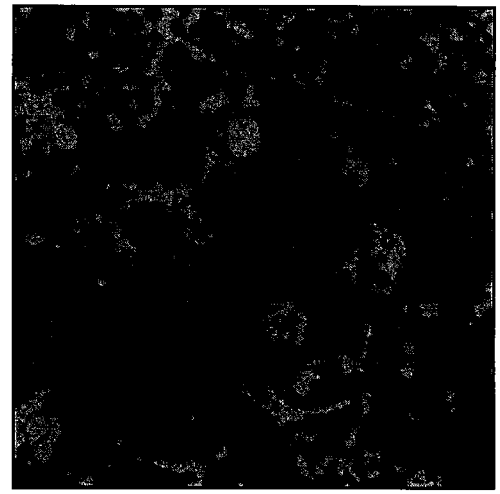
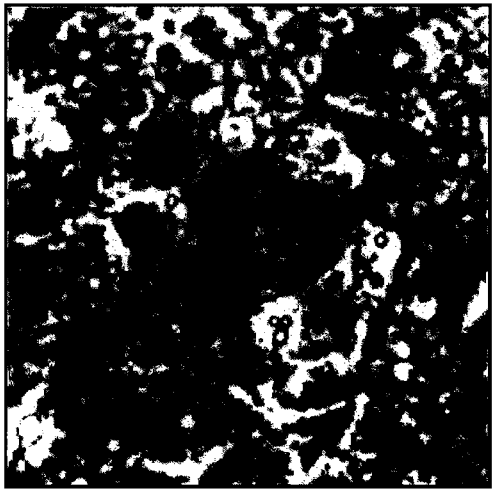

FIG. 6
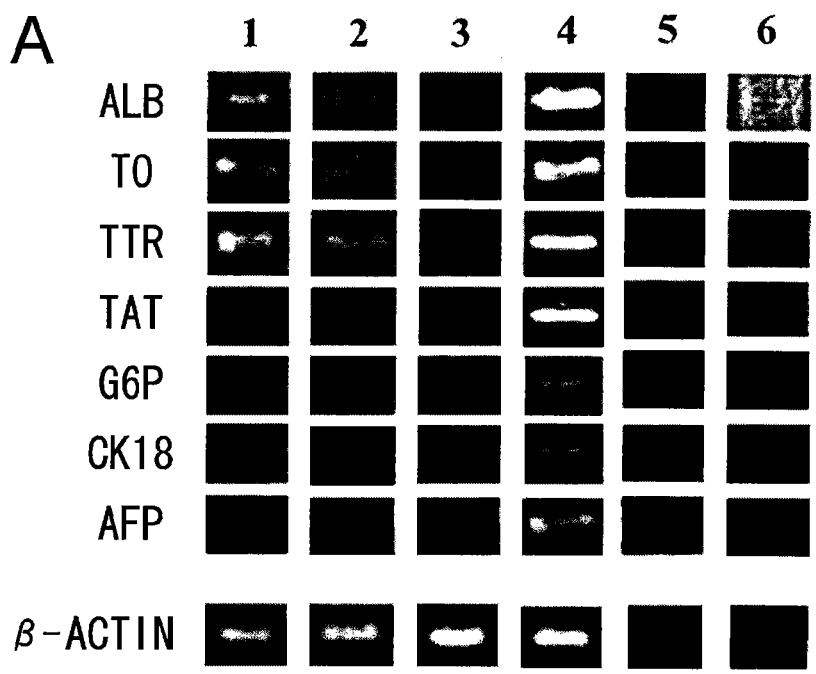
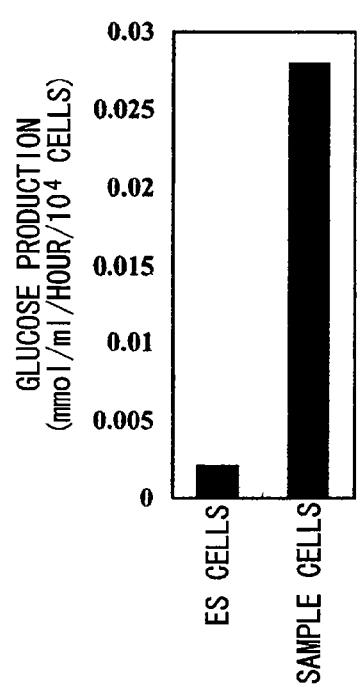
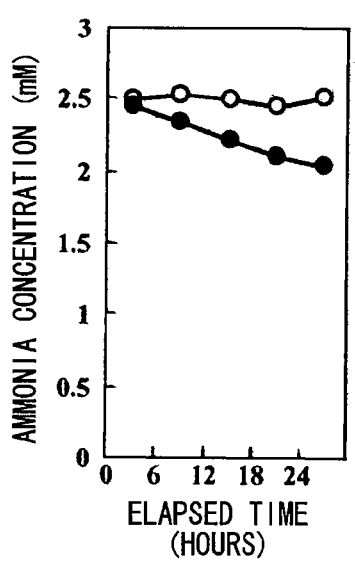

FIG. 7
HE STAINING　　　　GFP-POSITIVE CELLS
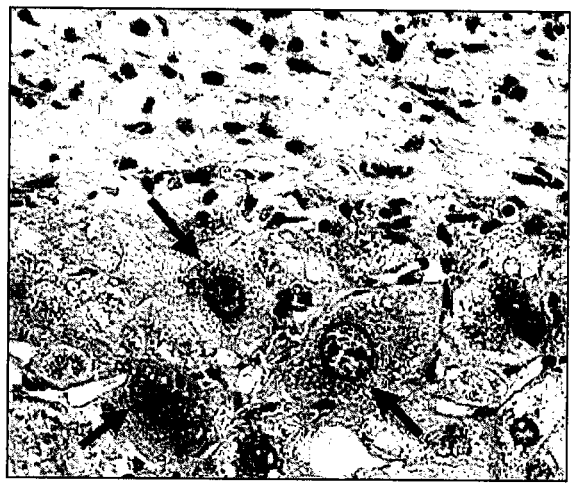 

FIG. 12
A
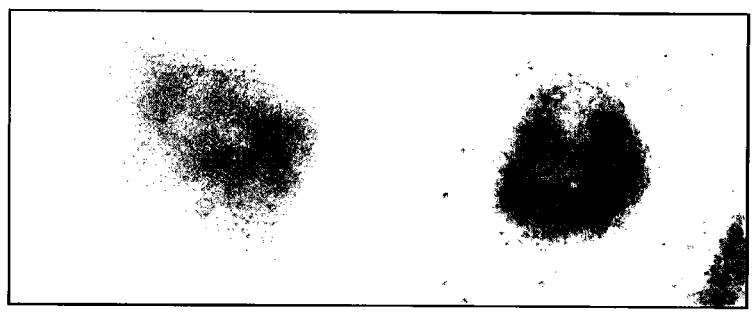
CMES/pALB-EGFP     NORMAL CMES
B
DAY 6
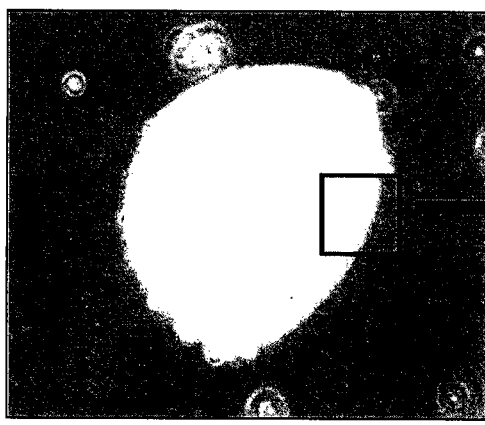
CMES/pALB-EGFP
AFTER 36 DAYS →
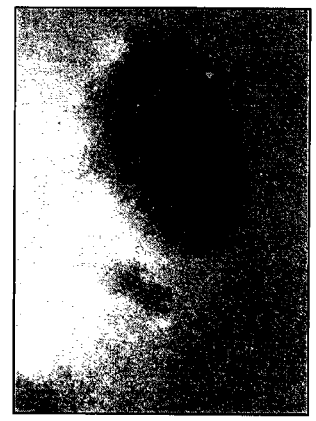
FLUORESCENT IMAGE

FIG. 13
A
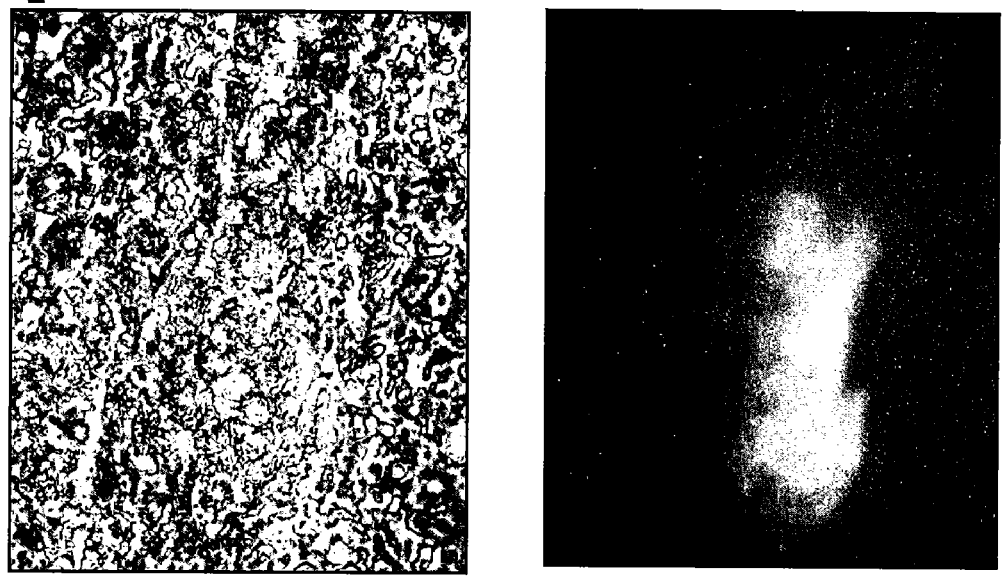
DAY 16
B
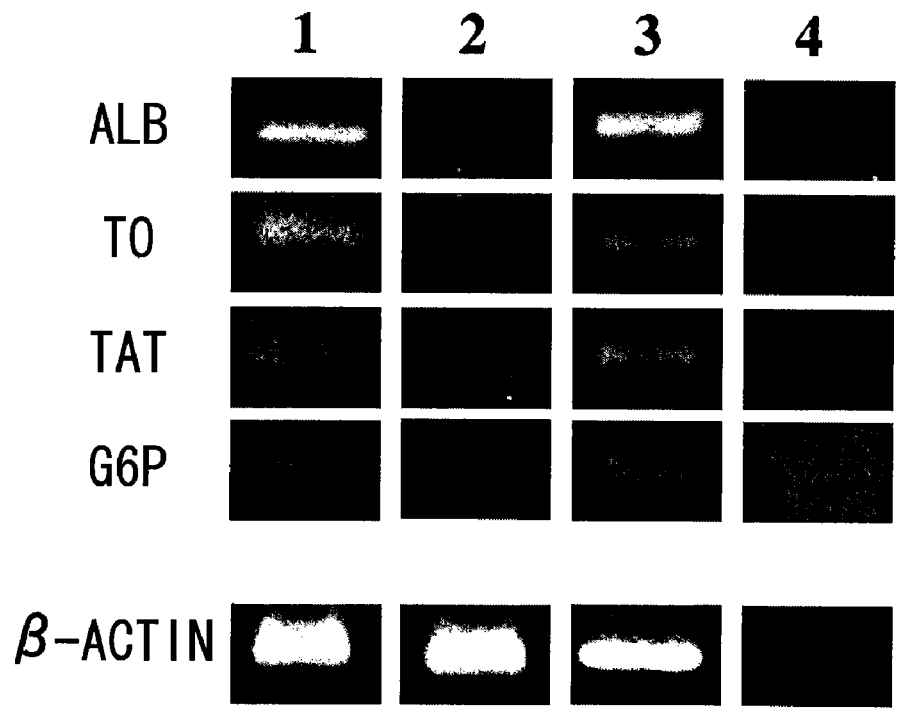

AGE: 18 YEARS
SEX: MALE
NUMBER OF PASSAGES: 2
POSITIVE: CD105, CD166, CD29, CD44
NEGATIVE: CD14, CD34, CD45

FIG. 15
A
B
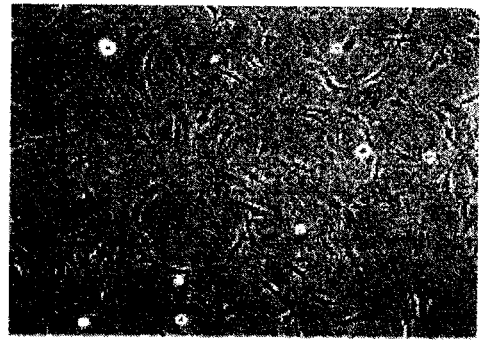
C
D

FIG. 17
A
B
C
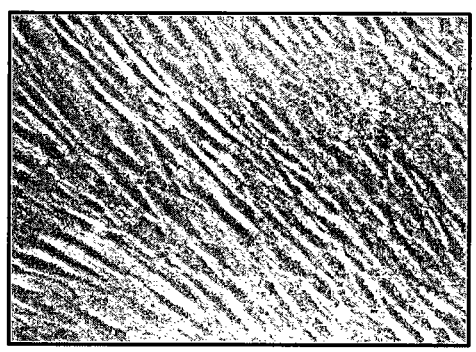
D

FIG. 19
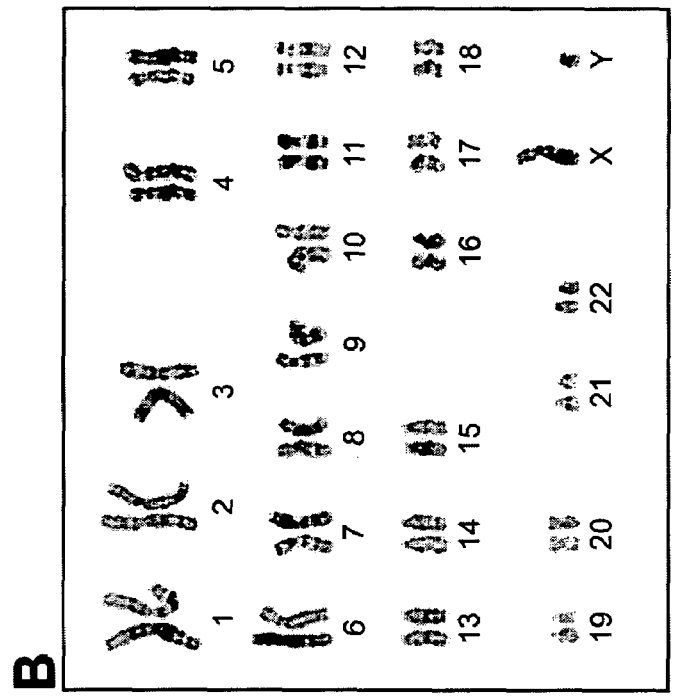
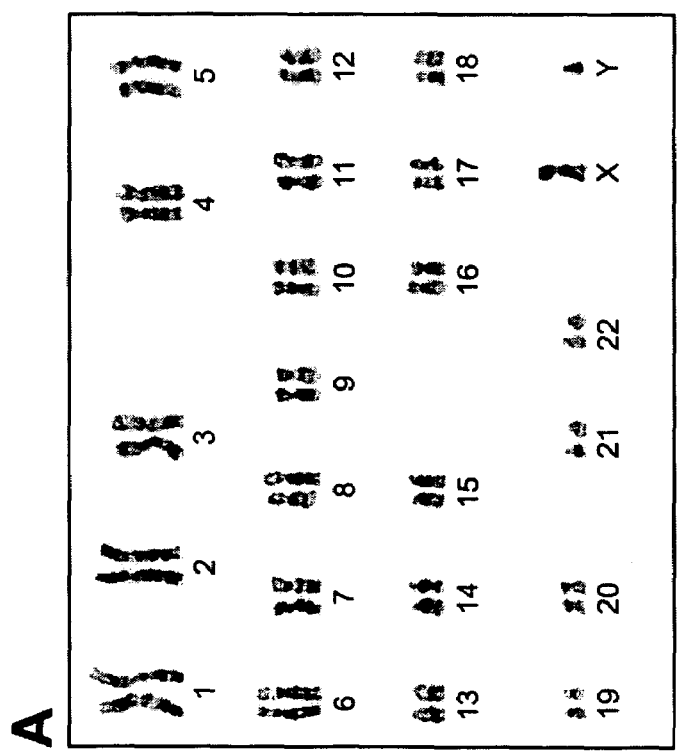

METHODS FOR INDUCING DIFFERENTIATION OF PLURIPOTENT CELLS

FIELD OF THE INVENTION

The present invention relates to methods for inducing differentiation of pluripotent cells.

BACKGROUND OF THE INVENTION

Interest in regeneration therapy is growing. Over the past few years, several studies have been conducted on the generation of hepatocytes using bone marrow and liver stem-like cells obtained from living bodies [Schwartz, R. E., Reyer, M., Koodie, L., Jiang, Y., Blackstad, M., Lund, T., Lenvik, T., Johnson, S., Hu, W. S., Verfaillie, C. M., "Multipotent adult progenitor cells from bone marrow differentiate into functional hepatocyte-like cells.", J. Clin. Invest. 109, 1291-1302, 2002; and Suzuki, A., Zheng, Y. W., Kaneko, S., Onodera, M., Fukao, K., Nakauchi, H., Taniguchi, H., "Clonal identification and characterization of self-renewing pluripotent stem cells in the developing liver.", J. Cell Biol. 156: 173-184, 2002]. At the same time, the present inventers observed that embryonic stem (ES) cells can differentiate. ES cells were first established by cloning cell lines that comprised several differentiation activities, using the inner cell masses of mouse blastocysts on dishes pre-treated with gelatin and comprising misogynic C-inactivated STO fibroblasts [Evans, M. J., Kaufman, M. H., "Establishment in culture of pluripotential cells from mouse embryos.", Nature 292:154-156, 1981; Martin, G. R., "Isolation of a pluripotent cell line from early mouse embryos cultured in medium conditioned by teratocarcinoma stem cells.", Proc. Natal. Aced. Sic. USA. 78: 7634-7638, 1981; and Bradley, A., Evans, M., Kaufman, M. H., Robertson, E., "Formation of germ-line chimaeras from embryo-derived teratocarcinoma cell lines.", Nature. 309: 255-256, 1984]. When in the presence of a feeder cell layer or leukemia inhibitory factor (LIF), ES cells multiply semi-permanently under conditions that maintain their undifferentiated state [Williams, R. L., Hilton, D. J., Pease, S. et al, "Myeloid leukaemia inhibitory factor maintains the developmental potential of embryonic stem cells.", Nature 336: 684-687, 1988]. When allowed to differentiate in a suspension culture, ES cells form spherical multi-cellular aggregates, called embryonic bodies (EBs). EBs have been shown to comprise a variety of cell populations. The processes of neuron, cardiac muscle and hematopoietic cell differentiation have been investigated using ES in vitro differentiation systems [Schmitt, R. M., Bruyns, E., and Snodgrass, H., "Hematopoietic development of embryonic stem cells in vitro, cytokine and receptor gene expression.", Genes Dev. 5: 728-740, 1991; Keller, G. M., "In vitro differentiation of embryonic stem cells.", Cur. Open. Cell Boil. 7: 862-869, 1995; Sanchez-Carpintero, R., and Narbona, J., "Executive system: a conceptual review and its study in children with attention deficit hyperactivity disorder.", Rev. Neurol. 33: 47-53, 2001; and Bain, G., Kitchens, D., Yao, M., Huettner, J. E., and Gottlieb, D. I., "Embryonic stem cells express neuronal properties in vitro.", Dev. Boil. 196: 342-357: 1995]. Thus, ES cell differentiation provides a valuable model for the study of visceral endoderm formation, and provides new possibilities for transplantation medicine.

Recently, biomaterials were used in the cell therapy of a number of daisies patients. For example, by culturing for four months in a medium supplemented with fibroblast growth factor (FGF)-2, ES cells transfected with hepatocyte nuclear factor (HNF)-3β were differentiated from albumin-induced cells [Ishizaka, S., Shiroi, A. et al., "Development of hepatocytes from ES cells after transfection with the HNF-3β gene.", FEBS J. 16: 1444-1446, 2002]. After 18 days of culture, EBs differentiated into hepatocytes, and were plated onto gelatin-coated dishes and incubated for 21 to 30 days without LIF and growth factors [Abe, K., Niwa, H., Iwase, K., Takiguchi, M., Mori, M., Abe, S., and Abe, K., "Endoderm-specific gene expression in embryonic stem cells differentiated to embryoid bodies.", Exp. Cell Res. 229: 27-34. 1996; and Miyashita, H., Suzuki, A., Fukao, K., Nakauchi, H., and Taniguchi, H., "Evidence for hepatocyte differentiation from embryonic stem cells in vitro.", Cell Transplantation. 11: 429-434, 2002]. The product of the EB-derived hepatocytes was plated on collagen type I-coated dishes and cultured for 18 days along with growth factors (acidic fibroblast growth factor (aFGF), hepatocyte growth factor (HGF), and oncostatin M (OsM)), dexamethasone, and IST (a mixture of insulin and transferin). However, in vitro EB formation was necessary in all cases where hepatocytes were formed from ES cells. Functional cells produced from EBs encounter several problems, such as teratoma formation. In addition, the formation of EBs from ES cells is laborious, and the differentiation rate is generally low. Differentiation to a number of other cells often occurs, thus calling for a hepatocyte purification Step. Few studies have attempted to differentiate cells from ES cells without mediating EBs. The only example of such a study is that in which Aubert et al induced nerve cell differentiation (Aubert, J., Dunstan, H., Chambers, I., and Smith, A., "Functional gene screening in embryonic stem cells implicates Wnt antagonism in neural differentiation.", 20: 1240-1245, 2002).

Mesenchymal stem cells (MSCs) were first isolated from bone marrow by Friedenstein in 1982 by simple plating on plastic in the presence of fetal calf serum (FCS) (Pittenger M. F. et al., Science 284, 143-147, 1999). Human MSCs isolated from bone marrow (BM) aspirates share a general immunophenotype, and are uniformly positive for SH2, SH3, CD29, CD44, CD71, CD90, CD106, CD120a and CD124, but negative for CD14, CD34, and the leukocyte common antigen CD45 (Pittenger F. M. et al., supra, 1999). In addition, the expression of VCAM-1, LFA-3, and HLA MHC Class I molecules in human MSCs was shown by flow cytometry analysis, suggesting the ability of these cells to undergo appropriate interaction with T-cells.

Human MSCs are multipotent, and they can differentiate into at least three lineages (osteogenic, chondrogenic, and adipogenic) when cultured under defined in vitro conditions (Pittenger F. M. et al., supra, 1999). Previously attempts at differentiation of mature hepatocytes from adult BM including human MSCs (CD34-positive cell fraction) have been reported (Camper S. A. and Tilghman S. M., Biotechnology 16, 81-87, 1991; Nahon J. L,. Biochimie. 69, 445-459, 1987; and Medvinsky A. and Smith A., Nature 422, 823-825, 2003). However, there are no reports of the induction of functional hepatocytes by direct differentiation in vitro.

SUMMARY OF THE INVENTION

The present invention was accomplished under the aforementioned circumstances. The objective of the present invention is to identify factors involved in inducing the differentiation of pluripotent cells, and to provide an efficient method of cell differentiation induction that utilizes these factors.

ES cells can differentiate into any adult animal cell type. It was recently demonstrated that ES cells could differentiate into hepatocytes. However, the mechanism serving as the basis of this differentiation is not fully understood. Previously, the present inventors found that mature hepatocytes can be formed using ES cells and a $CCl_4$-treated mouse strain (Yamamoto, H. et al., Hepatology, 37: 983-993, 2003). In the present invention, cDNA microarray technology was used to analyze changes in gene expression over 24 hours in placebo-treated mouse liver and $CCl_4$-treated mouse liver, and several growth factors were selected. Next, the effects of the matrix and growth factors on the differentiation rate of ES cells to hepatocytes were investigated. As a result, mouse ES cells were successfully differentiated into hepatocytes without forming EBs, using a simple adherent monoculture in a medium comprising several growth factors in culture dishes with two different matrices. Specifically, the expression of primary liver genes was determined, and liver-specific metabolic activities were measured in differentiated cells derived from mouse ES cells. These cells were demonstrated to have hepatocyte-specific characteristics. Moreover, hepatocytes were also successfully differentiated from the ES cells of cynomolgus monkeys. These results suggest that during differentiation into functional hepatocytes, ES cells require neither EB formation nor a co-culturing system. Furthermore, the present inventors discovered that transplantation of ES-derived hepatocytes exhibits a therapeutic effect against cirrhosis.

Furthermore, by utilizing the aforementioned differentiation inducing method, differentiation from human mesenchymal stem cells into mature hepatocytes was induced. Papers reporting the induction of differentiation of marrow cell-derived mesenchymal stem cells to hepatocytepapers have to date focused mostly on research using rat and mouse cells and individuals. There are few examples of inducing differentiation from human-derived cells. These few example cases of using human mesenchymal stem cells make use of the CD34 positive fraction, which is known to be an undifferentiation marker. On the other hand, the cells used by the present inventors herein are CD34 negative. Previously, induction of differentiation into cardiac muscle, skeletal muscle, bone, nerve cells, epithelial cells and the like has been confirmed using demethylating agents, etc. However, there has been no example reports of the induction of differentiation into hepatocytes. However, results obtained using the present differentiation inducing system revealed that the CD34 negative fraction also comprises the ability of differentiating into hepatocytes. In addition, the expression of an important liver gene was confirmed in cells differentiated using the present method. Also, the differentiated cells derived from human mesenchymal stem cells using the present method comprised characteristics particular to hepatocytes. Furthermore, chromosome abnormality was not found to be caused, regardless of the presence or absence of differentiation induction.

In this manner, the present invention provides evidence of serving as a novel source of hepatocytes for new therapeutic strategies such as cell transplantation and tissue manipulation.

Specifically, the present invention provides the following:

[1] a method for inducing differentiation of pluripotent cells comprising the following steps (a) and (b):
(a) culturing the pluripotent cells in a medium comprising any one of the following growth factors (i) to (iii):
   (i) acidic fibroblast growth factor, fibroblast growth factor 4, and hepatocyte growth factor;
   (ii) acidic fibroblast growth factor, and growth factor(s) selected from activin A, epidermal growth factor, and β-nerve growth factor; and
   (iii) fibroblast growth factor 4, and growth factor(s) selected from activin A and hepatocyte growth factor; and,
(b) culturing the cell cultured in step (a) in a medium comprising oncostatin M;

[2] the method according to [1], wherein a gelatin-coated culture dish is used in step (a), and a collagen type I-coated culture dish or laminin-coated culture dish is used in step (b);

[3] the method according to [1], wherein a collagen type I-coated culture dish is used;

[4] a method for inducing differentiation of pluripotent cells comprising the following steps (a) and (b):
(a) culturing the pluripotent cells in a medium comprising at least one growth factor selected from retinoic acid, leukemia inhibitory factor, and hepatocyte growth factor; and,
(b) culturing the cell cultured in step (a) in a medium comprising any one of the following growth factors (i) to (iii):
   (i) acidic fibroblast growth factor, fibroblast growth factor 4, and hepatocyte growth factor;
   (ii) acidic fibroblast growth factor, and growth factor(s) selected from activin A, epidermal growth factor and β-nerve growth factor; and
   (iii) fibroblast growth factor 4, and growth factor(s) selected from activin A and hepatocyte growth factor;

[5] the method according to [3], wherein gelatin-coated culture dishes are used in steps (a) and (b);

[6] a method for inducing differentiation of pluripotent cells comprising the following steps (a) to (c):
(a) culturing the pluripotent cells in a medium comprising at least one of the growth factors selected from retinoic acid, leukemia inhibitory factor and hepatocyte growth factor;
(b) culturing the cell cultured in step (a) in a medium comprising any one of the following growth factors (i) to (iii):
   (i) acidic fibroblast growth factor, fibroblast growth factor 4 and hepatocyte growth factor;
   (ii) acidic fibroblast growth factor, and growth factor(s) selected from activin A, epidermal growth factor and β-nerve growth factor; and
   (iii) fibroblast growth factor 4, and growth factor(s) selected from activin A and hepatocyte growth factor; and,
(c) culturing the cells cultured in step (b) in a medium comprising oncostatin M;

[7] the method according to [5], wherein gelatin-coated culture dishes are used in steps (a) and (b), and a collagen type I-coated culture dish or laminin-coated culture dish is used in step (c);

[8] a method according to any one of [1] to [7], wherein the pluripotent cells are derived from a mammal;

[9] the method according to [8], wherein the mammal is a human, monkey, mouse, rat or pig;

[10] a method according to any one of [1] to [9], wherein the pluripotent cells are embryonic stem cells, adult stem cells, mesenchymal stem cells, or umbilical cord blood cells;

[11] a method for producing hepatocytes, wherein the method comprises steps (a) and (b) according to any one of [1] to [5], or steps (a) to (c) according to [6] or [7];

[12] the method according to [11], wherein the hepatocytes are mature hepatocytes;

[13] the method according to [11] or [12], wherein the pluripotent cells are derived from a mammal;

[14] the method according to [13], wherein the mammal is a human, monkey, mouse, rat or pig;

[15] a method according to any one of [11] to [14], wherein the pluripotent cells are embryonic stem cells, adult stem cells, mesenchymal stem cells, or umbilical cord blood cells;

[16] a hepatocyte produced by a method according to any one of [11] to [15];

[17] a therapeutic agent for a liver disease comprising the hepatocyte according to [16];

[18] the therapeutic agent according to [17], wherein the liver disease is cirrhosis, fulminant hepatitis, biliary atresia, liver cancer, or hepatitis;

[19] a kit comprising any one of the following (a) to (c):
(a) acidic fibroblast growth factor, fibroblast growth factor 4, and hepatocyte growth factor;
(b) acidic fibroblast growth factor, and growth factor(s) selected from activin A, epidermal growth factor, and β-nerve growth factor; and
(c) fibroblast growth factor 4, and growth factor(s) selected from activin A and hepatocyte growth factor;

[20] the kit according to [19] further comprising oncostatin M; and

[21] the kit according to [20] further comprising at least one growth factor selected from the group consisting of retinoic acid, leukemia inhibitory factor, and hepatocyte growth factor.

BRIEF DESCRIPTION OF THE DRAWINGS

FIG. 2 shows graphs indicating the effects of growth factors on the ability to induce GFP-positive cells. (A): A single growth factor (white bars: RA-untreated ES cells, black bars: RA-treated ES cells). (B), (C) and (D): Combinations of two growth factors. (E): Combinations of three growth factors. The final growth factor concentrations are described in the Examples. (B) and (E) depict pre-culturing for three days in media comprising RA in the presence of LIF. Percentages are indicated as average scores (HGF, FGF4 and aFGF: n=5, others: n=2).

FIG. 3 shows photographs depicting GFP-positive cells visualized with a fluorescence microscope. (A) and (B): cells on collagen type I-coated dishes; (C): cells on a gelatin-coated dish; (D) cells on a laminin-coated dish; (E) cells on a fibronectin-coated dish; and (F) cells on a vitronectin-coated dish. The collagen type I-coated and gelatin-coated dishes were obtained from Iwaki (Tokyo, Japan), while the laminin-coated, fibronectin-coated and vitronectin-coated dishes were produced from bacterial culture dishes as described in the Examples (ATG, Tokyo, Japan). Several scores showed the highest rate of GFP-positive cells in each matrix coated-dishes (n=5). The original magnification factor was ×20.

FIG. 5 depicts photographs showing GFP expression during ES cell differentiation. (A) Cells using a fluorescence microscope. (B) Cells using a phase microscope. (C) A combination of (A) and (B) using PhotoShop 5.0 (Adobe).

FIG. 6 depicts a photograph and graphs showing analysis of hepatocyte-specific marker gene expression and metabolic activity in differentiated ES cells, cultured in vitro. (A) The expression of differentiated hepatocyte-specific marker genes. Lane 1: Differentiated ES cell fraction (7 days); lane 2: differentiated ES cell fraction (5 days); lane 3: untreated ES cells; lane 4: positive control (ALB, TO, TTR, TAT, CK18, G6P and β-actin from mouse liver, and AFP from HepG2); lane 5: no template; and lane 6: genomic DNA from untreated ES cells. (B) Analysis of ES cell differentiation with respect to glucose level in culture supernatant (one day after plating). (C) Investigation of the differentiation of ES cells (•) with respect to ability to remove ammonia from culture (one day after plating). pALB/EGFP cells (-) were used as the control. (B) and (C) show average scores (n=2).

FIG. 7 depicts photographs showing GFP-positive hepatocytes located near liver cirrhosis sites.

FIG. 12 depicts photographs showing (A) alkaline phosphatase activity of pALB-EGFP/CMES cells, and (B) the ability to form embryoid bodies (EBs).

FIG. 13 depicts photographs analyzing GFP-positive cells induced to differentiate from CMES cells in vitro. (A) Left: cells using a phase microscope; right: cells using a fluorescence microscope. (B) Expression of hepatocyte-specific marker genes. Lane 1: cDNA of the GFP-positive fraction of pALB-EGFP/CMES cells; lane 2: cDNA of undifferentiated pALB-EGFP/CMES cells; lane 3: cDNA of CM hepatocytes; and lane 4: genomic DNA corresponding to the cDNA of pALB-EGFP/CMES cells.

FIG. 15 shows photographs of the results of investigation regarding drug sensitivity to genestin of normal human mesenchymal stem cells in which genes were not introduced. Neomycin concentrations were: (A) 0 μg/ml, (B) 50 μg/ml, (C) 100 μg/ml and (D) 200 μg/ml. Object lens×20. According to the experimental results, the concentration of neomycin was determined to be 200 μg/ml.

FIG. 17 shows photographs obtained by using a fluorescence microscope to visualize the effect of inducing pALB/hMSC differentiation to GFP positive cells in the presence or the absence of HIFC addition. (A) A phase contrast microscope image of pALB/hMSCs subjected to HIFC treatment; (B) a fluorescence microscope image of pALB/hMSCs subjected to HIFC treatment; (C) a phase contrast microscope image of pALB/hMSCs not subject to HIFC treatment; and (D) a fluorescence microscope image of pALB/hMSCs not subject to HIFC treatment. GFP positive cells were only detected in cells subjected to HIFC treatment (GFP positive rate: 70% or higher). No GFP positive cells were detected in cells not subjected to HIFC treatment. The presence or absence of HIFC was also confirmed to change form (day 14). Object lens×20.

FIG. 19 is photographs showing pALB/hMSC chromosomes in the presence or absence of HIFC treatment. (A) HIFC-untreated pALB/hMSC chromosomes; and (B) HIFC-treated and differentiation-induced pALB/hMSC choromosomes (day 14). The number of each chromosome is indicated by the figure written beneath. Chromosome abnormality was not detected, regardless of the presence or absence of differentiation (n=30).

DETAILED DESCRIPTION OF THE INVENTION

Figure 1:
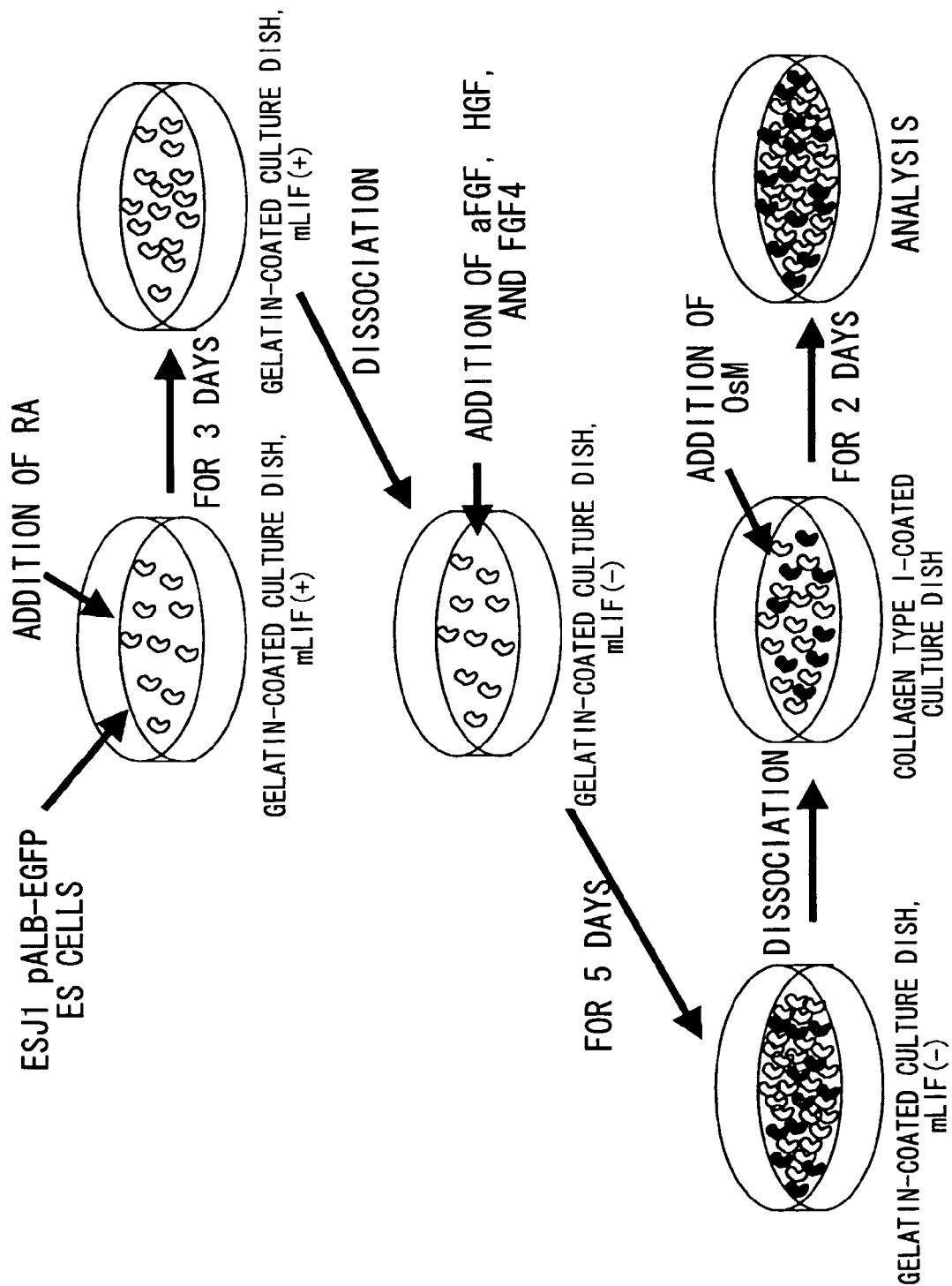
FIG. 1 shows in vitro induction of ES cell differentiation. The protocol for in vitro differentiation used in the present invention is as described in Examples.

The differentiation of pluripotent cells can be efficiently induced by the present invention. In particular, the present invention has the advantage of being able to induce ES cell differentiation without EB formation.

The combination of cell growth factors developed (discovered) by the present inventors was for the first time confirmed to be applicable not only to ES cells but also to marrow cell-derived mesenchymal stem cells. In addition, the hepatic induction factor cocktail (HIFC) differentiation inducing system developed by the present inventors has a high differentiation efficiently, uses only known substances which can be industrially produced, and induces differentiation to mature hepatocytes using only an in vitro system. Therefore this system can prevent infection by unknown viruses, or the problem of rejection reactions. Furthermore, since the cells return to a living body after differentiation has been induced, this system also overcomes anxieties regarding fusion with host cells accompanied with differentiation induction. Thus, the present system is a very important technique aiming at clinical application in humans.

Furthermore, kits of the present invention can be used to produce hepatocytes that can be used as therapeutic agents for liver diseases, and as research reagents for inducing the differentiation of pluripotent cells.

The present invention provides methods for inducing the differentiation of pluripotent cells. Using the methods of the present invention, it is possible to induce the differentiation of pluripotent cells in vitro, without utilizing the tissue regeneration ability of individual animals in which a disease has been artificially induced (e.g., mice). Since conventional methods (Yamamoto, H. et al., Hepatology, 2003) utilize the tissue regeneration ability of individual animals in which a disease has been artificially induced, problems such as ethical issues including animal care, and the potential for infection by unknown pathogens are encountered. However, these problems are not present in the methods for differentiation induction developed by the present inventors. In the present invention, none of the steps use animals. In addition, in the present invention, differentiation of induction is aseptic, and the origins of all required materials are clearly defined.

Use of a method of the present invention allows differentiation of ES cells to be induced without EB formation. In cell differentiation methods that use EB formation, various differentiations occur all at once, and thus there are few endodermally-differentiated cells, and only a portion of these differentiate into hepatocytes. Therefore, a high rate of hepatocyte induction is unlikely. By using a method of the present invention, hepatocytes can be obtained from ES cells extremely efficiently. Herein, EBs refer to "ES cell-derived cell clusters with the previously described phenomena and properties". EBs are formed as follows: ES cells are cultured in a medium comprising mouse fibroblasts and LIF; cells maintaining pluripotency are recovered from culture dishes; the mouse fibroblasts and LIF are removed; the ES cells are additionally cultured on non-matrix-coated culture dishes, where they form clusters (cell clusters) when suspended in the culture medium; and various cell differentiations (to any of the three embryonic germ layers) begin spontaneously and irregularly in these cell clusters.

A method of the present invention comprises the step of culturing pluripotent cells in a medium comprising any one of the following growth factors (i) to (iii) (step (a)):

(i) acidic fibroblast growth factor (aFGF), fibroblast growth factor 4 (FGF4), and hepatocyte growth factor (HGF);

(ii) FGF, and growth factor(s) selected from activin A, epidermal growth factor (EGF), and β-nerve growth factor (βNGF); and (iii) FGF4, and growth factor(s) selected from activin A and HGF.

In the present invention, differentiation of pluripotent cells can be induced more efficiently by using the growth factors described in (i). Herein, "acidic fibroblast growth factor (aFGF)" may be referred to as "fibroblast growth factor 1 (FGF1)".

In the present invention, examples of pluripotent cells include embryonic stem cells (ES cells), adult stem cells, mesenchymal stem cells and umbilical cord blood cells, however, any cell which has the ability to differentiate into various types of cells can be included as a pluripotent cell of the present invention.

In addition, examples of biological species from which the pluripotent cells of the present invention can be derived include, but are not limited to, preferably mammals, and more preferably primates, rodents and artiodactyls, such as humans, monkeys, mice, rats, and pigs. Pluripotent cells can be induced to differentiate even if the biological species from which the cells are derived differs from the biological species from which the growth factors are derived. For example, differentiation can be induced in cynomolgus monkey ES cells and mouse ES cells by using human-derived growth factors.

A method of the present invention comprises the step of culturing the cells cultured in step (a) in a medium comprising oncostatin M (step (b)).

In a method of the present invention, pluripotent cells may also be pre-cultured prior to step (a) in a medium comprising at least one growth factor selected from retinoic acid (RA), leukemia inhibitory factor (LIF) and HGF. By carrying out this pre-culturing step, differentiation of pluripotent cells can be induced more efficiently. In this pre-culturing step, pluripotent cells can be induced to differentiate more efficiently by culturing in a medium comprising RA in addition to LIF and/or HGF. When using human cells as pluripotent cells, the cells can be induced to differentiate more efficiently even without a pre-culturing step.

The cell culturing methods of the present invention include a two-dimensional culturing method, using culture dishes coated with different matrices, or culture dishes coated or not coated with a matrix. It may also be a three-dimensional culturing method, using a soft gel such as Matrigel or a collagen sponge, or it may be a combination of the two. However, it is preferably a two-dimensional culturing method, using culture dishes coated with different matrices, or culture dishes coated or not coated with a matrix. More preferably, it is a two-dimensional culturing method in which gelatin-coated culture dishes are used in the pre-culturing step and step (a), and collagen type I-coated culture dishes or laminin-coated culture dishes are used in step (b). When using human cells as pluripotent cells, collagen type I-coated culture dishes are preferably used.

Although the Examples of the present invention disclose detailed culturing conditions for steps (a), (b), and the pre-culturing step, the culturing conditions in the methods of the present invention are not limited to these specific conditions, and any typically acceptable culturing conditions may be employed. For example, $5.0 \times 10^3$ to $5.0 \times 10^6$ cells/culture dish is an exemplary number of cells to start differentiation induction. Exemplary periods for differentiation induction are two to ten days (preferably five days) in step (a), one to four days (preferably two days) in step (b), and two to five days (preferably three days) in the pre-culturing step. The time period for induction of differentiation in human mesenchymal cells is 12 to 21 days (preferably 14 days).

Examples of growth factors according to the present invention include, but are not limited to, RA (all-trans-retinoic acid: Wako Pure Chemical Industries, Ltd.), LIF (ESGRO™ ($10^7$ units): Funakoshi Co., Ltd.), HGF (Human HGF: Veritas Corporation), aFGF (Human FGF-acidic: Veritas Corporation), FGF4 (Human FGF-4: Veritas Corporation) and OsM (Human oncostatin M: Veritas Corporation).

In the present invention, cell differentiation can also be induced by carrying out the pre-culturing step and step (a). In this case, cells are preferably cultured in a medium comprising RA added to LIF and/or HGF in the pre-culturing step, however, cells can be induced to differentiate even if cultured in other media, such as media comprising only LIF, only HGF, or both LIF and HGF. Moreover, cell differentiation can also be induced even when cells are cultured in a medium comprising only HGF in the pre-culturing step, and then directly transferred to step (b) Such methods are also provided by the present invention.

In the present invention, hepatocytes, and particularly mature hepatocytes, can be produced using the aforementioned methods for differentiation induction. Obtaining finally differentiated cells from ES cells is extremely useful in research on hepatocyte development and differentiation, and in research on and elucidation of hepatocyte intermediate differentiation pathways. Mature hepatocytes may be used for cell transplant therapy objectives. Since immature hepatocytes are not fully differentiated, their latent potential for abnormal differentiation or abnormal proliferation (e.g., canceration) is thought to be higher than for mature hepatocytes. Thus the acquisition of mature hepatocytes is also advantageous from this point of view.

To confirm whether or not differentiated cells are hepatocytes, hepatocyte markers or hepatocyte functions can be used as indexes. Examples of hepatocyte functions include the ability to produce glucose and the ability to metabolize ammonia. The ability to produce glucose can be confirmed using the glucose oxidase method to analyze glucose levels in the culture supernatant. The ability to metabolize ammonia can be confirmed using the modified indophenol method to analyze ammonia levels in the culture medium (Horn, D. B. & Squire, C. R., Chim. Acta. 14: 185-194, 1966).

The present invention also provides hepatocytes produced according to the aforementioned steps. These hepatocytes can be used to treat liver diseases. For example, liver diseases can be treated using a method wherein hepatocytes are directly transplanted through the hepatic portal, or a method wherein hepatocytes are transplanted after embedding in collagen, polyurethane or another known biocompatible material. In this manner, the present invention also provides uses for hepatocytes produced according to the aforementioned steps. More specifically, the present invention provides liver disease therapeutic agents that comprise hepatocytes. In addition, the present invention also provides methods of treating liver diseases using hepatocytes. Examples of liver diseases of the present invention include, but are not limited to, cirrhosis, fulminant hepatitis, biliary atresia, liver cancer, and hepatitis (e.g., viral hepatitis or alcoholic hepatitis).

In addition, the present invention provides a kit comprising (i) aFGF, FGF4, and HGF; (ii) aFGF, and growth factor(s) selected from activin A, EGF, and βNGF; or (iii) FGF4, and growth factor(s) selected from activin A and HGF. Moreover, the present invention also provides a kit comprising OsM and any of the factors of (i) to (iii); a kit comprising OsM, LIF, RA, and any of the factors of (i) to (iii); a kit comprising OsM, HGF, RA, and any of the factors of (i) to (iii); a kit comprising OsM, LIF, HGF, RA, and any of the factors of (i) to (iii); a kit comprising OsM, RA, and any of the factors of (i) to (iii); a kit comprising OsM, LIF, and any of the factors of (i) to (iii); a kit comprising OsM, HGF, and any of the factors of (i) to (iii); or a kit comprising OsM, LIF, HGF, and any of the factors of (i) to (iii).

These useful kits can be utilized in the methods of the present invention. Kits of the present invention can be used for the production of hepatocytes useful as therapeutic agents for liver diseases. They can also be used as research reagents for inducing the differentiation of pluripotent cells. For example, mixtures of differentiation induction factors for use in each step of a method of the present invention can be respectively enclosed in water-soluble capsules, and these capsules added in proportion to the amount of culture medium. According to the kit user's research objectives, the concentrations of differentiation induction factors in the culture medium can be adjusted using the amount of mixed capsules added, and the volume of differentiation-inducing culture medium can be changed according to the required number of cells. In addition, each step can be continued or terminated by preparing mixed capsules of differentiation induction factors that correspond to each step. When used together with culture conditions that allow two-dimensional culturing using culture dishes coated with different matrices (including culture dishes without a matrix coating), or three-dimensional culturing using a soft gel such as Matrigel, a collagen sponge, or such, the present invention enables, without time constraints and in any manner desired, (i) the real time observation of the differentiation induction status (including cell morphology, tissue reconfiguration, and changes in gene and protein expression) of pluripotent cells which can differentiate either two- or three-dimensionally, and (ii) experimentation with these cells. By combining products currently available on the market, this differentiation induction system can be packaged as a kit. Therefore, the differentiation induction system of the present invention can be used industrially, and the production of kits is also beneficial for use as research reagents.

Herein below, the present invention will be specifically described using Examples, however, is not to be construed as being limited thereto.

(1) cDNA Microarray Analysis of Gene Expression Between Placebo-Treated and $CCl_4$-Treated Mice 129SVJ strain mice were treated with $CCl_4$ in olive oil, and control (placebo) mice were treated only with olive oil. After 24 hours, RNA was extracted from the livers of these mice, and microarray analysis was carried out on DNA chips comprising 12,488 cDNA clones. The arrays were scanned with an Affymetrix GeneChip scanner, and primary image analysis was performed using Microsoft Excel.

(2) ES Cell Cultures

The ES cell line ESJ1 (129SVJ strain) was maintained in an undifferentiated state in gelatin-coated dishes (IWAKI, Tokyo, Japan) in 400 ml of Dulbecco's modified Eagle medium containing 20% fetal bovine serum, 5 ml of non-essential amino acids, 5 ml of 100× nucleosides stock solution (4 mg of adenosine, 4.25 mg of guanosine, 3.65 mg of cytidine, 3.65 mg of uridine, and 1.2 mg of thymidine), 5 ml of antibiotic-antimycotic solution (GIBCO BRL, Funakoshi Co., Ltd., Tokyo, Japan), 3.5 µl of β-merucaptoethanol, 1000 unit/ml of recombinant mouse leukemia inhibitory factor (LIF) (ESGRO, Funakoshi Co., Ltd., Tokyo, Japan) and 175 µg/ml of G418 in a 5% $CO_2$ incubator. To stimulate expression of the EGFP transgene in hepatocytes, an albumin promoter/enhancer plasmid named pALB-EGFP was constructed [Quinn, G. et al., Res. Commun. 276: 1089-1099, 2000]. Albumin expression was evaluated using the fluorescence activity of green fluorescent protein (GFP). Intense signals observed in HepG2 cell promoters (hepatoblastoma) indicated that the pALB-EGFP (enhanced green fluorescent protein) construct acted as an indicator of hepatic differentiation of ES cells. G418-resistant pALB-EGFP/ES cells were prepared and cultured as described [Quinn, G. et al., Res. Commun. 276: 1089-1099, 2000]. When these cells differentiated to albumin-producing cells, such as hepatocytes, they could be detected as GFP-expressing cells. By using such cells, differentiated cells can be quantified by sorting using flow cytometry, and then determining the amount of GFP.

(3) In Vitro ES Cell Differentiation

To induce differentiation, $5.0 \times 10^5$ ES cells were cultured at 37° C. for three days using gelatin-coated dishes with LIF and $1.0 \times 10^{-8}$ M all-trans retinoic acid (RA) (Wako Pure Chemical Industries, Ltd., Tokyo, Japan). Next, $5.0 \times 10^4$ pre-cultured ES cells were plated on gelatin-coated culture dishes, incubated at 37° C. for five days, and then dissociated from the dish. Some of these cells were transferred to several coated dishes, followed by additional culturing at 37° C. for two days in a medium comprising Human oncostatin (OsM) (Veritas Corporation, Tokyo, Japan) (FIG. 1). Media were changed every day. In some experiments, growth factors were added into culture media (100 ng/ml of acidic fibroblast growth factor (aFGF), 20 ng/ml of basic fibroblast growth factor (bFGF), 50 ng/ml of hepatocyte growth factor (HGF), 20 ng/ml of fibroblast growth factor-4 (FGF-4), 10 ng/ml OsM, 100 ng/ml β-nerve growth factor (β-NGF), 100 ng/ml epithelial growth factor (EGF), and 2 ng/ml activin A (Veritas Corporation, Tokyo, Japan)).

(4) Analysis of Alkaline Phosphatase Activity

RA-treated ES cells were fixed in 4% paraformaldehyde for ten minutes, and in 100% EtOH for ten minutes. The cells were then washed with $H_2O$ for 30 minutes. Alkaline phosphatase activity was detected using a Vector Red Alkaline Phospharase Substrate Kit I (Funakoshi Co., Ltd., Tokyo, Japan), according to kit instructions.

(5) RT-PCR Analysis

Total RNA was extracted by using ISOGEN (Nippon Gene Co. Ltd., Tokyo, Japan). Single-stranded cDNA was synthesized in solution of total volume 20 µl, containing 2 µg of total RNA, 0.5 µl of oligo $(dT)_{18}$ primer, 10 pmol of dNTPs, five units of RAV-2 RTase, and first Strand Synthesis buffer (TaKaRa Bio Inc., Kyoto, Japan). Synthesis was performed at 36° C. for ten minutes, 42° C. for one hour, 56° C. for ten minutes, and 99° C. for five minutes. Primers were synthesized as follows (bracketed information: sense primer, anti-sense primer, annealing temperature, PCR cycles, and length of the amplified fragment):

```
albumin ALB
(5'-GCTACGGCACAGTGCTTG-3';         (SEQ ID NO: 1)
5'-CAGGATTGCAGACAGATAGTC-3';       (SEQ ID NO: 2)
60° C.; 50 cycles; 260 bp), tryptophan 2,3-dioxygenase
(TO)
(5'-TGCGCAAGAACTTCAGAGTGA-3';      (SEQ ID NO: 3)
5'-AGCAACAGCTCATTGTAGTCT-3';       (SEQ ID NO: 4)
56° C.; 50 cycles; 419 bp), tranthyretin (TTR)
(5'-CTCACCACAGATGAGAAG-3';         (SEQ ID NO: 5)
5'-GGCTGAGTCTCTCAATTC-3';          (SEQ ID NO: 6)
55° C.; 50 cycles; 225 bp), tyrosine aminotransferase (TAT)
(5'-ACCTTCAATCCCATCCGA-3';         (SEQ ID NO: 7)
5'-TCCCGACTGGATAGGTAG-3',          (SEQ ID NO: 8)
50° C.; 50 cycles; 206 bp), α-fetoprotein (AFP)
(5'-TCGTATTCCAACAGGAGG-3';         (SEQ ID NO: 9)
5'-AGGCTTTTGCTTCACCAG-3';          (SEQ ID NO: 10)
55° C.; 25 cycles; 173 bp), glucose-6-phosphatase (G6P)
(5'-TGATTGCTGACCTGAGGAAC-3';       (SEQ ID NO: 11)
5'-CAAACACCGGAATCCATACG-3';        (SEQ ID NO: 12)
62° C.; 50 cycles; 352 bp), cytokeratin 18 (CK18)
(5'-TGGTACTCTCCTCAATCTGCTG-3';     (SEQ ID NO: 13)
5'-CTCTGGATTGACTGTGGAAGTG-3';      (SEQ ID NO: 14)
60° C.; 50 cycles; 382 bp) and β actin
(5'-AGAGCAAGAGAGGTATCCTG-3';       (SEQ ID NO: 15)
5'-AGAGCATAGCCCTCGTAGAT-3';        (SEQ ID NO: 16)
55° C.; 25 cycles; 339 bp).
```

Amplification was performed in a total volume of 50 µl, containing 4 µl of cDNA as a template, 100 µM of dNTPs, 10 pmol of primers, 1.0 unit of Ex-Taq, and Ex-Taq buffer (TaKaRa Bio Inc., Kyoto, Japan). After PCR, aliquots were run on 3.0% agarose gels, stained with ethidium bromide (EtBr), and photographed under UV illumination.

(6) Biochemical Analyses of ES-Derived Hepatocytes

Glucose levels in the culture supernatant were analyzed for cultured GFP-positive cell fractions, using the glucose oxidase method, as previously described [Sistare, F. D. et al., J. Biol. Chem. 260: 12748-12753, 1985]. To examine cellular ammonia detoxification activity, GFP-positive cell fractions were cultured in DMEM comprising 2.5 mM $NH_4Cl$, and further incubated for 24 hours. Using the modified indophenol method, culture media were tested for NH$_4$Cl concentration at 0, 6, 12, 18 and 24 hours after culture initiation [Horn, D. B. & Squire, C. R., Chim. Acta. 14: 185-194, 1966].

All patents, published patent applications, and publications cited herein are incorporated by reference in their entirety.

EXAMPLE 1 cDNA Microarray Analysis

The present inventors used a cDNA microarray to analyze growth factor genes which are expressed differently in CCl$_4$-treated mouse liver and placebo-treated mouse liver (Table 1).

TABLE 1

| Accession number | Gene name | CCl$_4$-untreated | CCl$_4$-treated | Fold change |
|---|---|---|---|---|
| Y00848 | Fibroblast growth factor 3 | −128.3 | 82.7 | ~1.3 |
| X14849 | Fibroblast growth factor 4 | 140.9 | 331.5 | 2.4 |
| M37823 | Fibroblast growth factor 5 | −219.9 | 210.4 | ~1.6 |
| D12483 | Fibroblast growth factor 8 | −180.3 | 165.0 | ~1.7 |
| D89080 | Fibroblast growth factor 10 | −483.5 | 345.7 | ~2.1 |
| AF020737 | Fibroblast growth factor 13 | 13.1 | 138.0 | ~1.7 |
| AB004639 | Fibroblast growth factor 18 | −101.8 | 1.3 | ~1.0 |
| X72307 | Hepatocyte growth factor | −19.0 | 196.6 | ~1.8 |
| D63707 | Hepatoma-derived growth factor | 5718.3 | 12635.9 | 2.2 |
| M17298 | β-nerve growth factor | −41.2 | 372.9 | ~2.6 |
| X04480 | Insulin-like growth factor 1 | 8120.7 | 42535.0 | 5.2 |
| X71922 | Insulin-like growth factor 2 | −41.7 | 71.1 | ~1.3 |
| K01668 | Mast cell growth factor | 46.5 | 95.6 | 2.1 |
| M92420 | Transforming growth factor α | 79.5 | 394.7 | ~2.6 |
| NM_021438 | Fibroblast growth factor 1 | 575.9 | 1046.2 | 1.8 |

Genes are listed by GenBank accession number. Fold difference in gene expression was measured using analyzer software.
~ A new expression gene in the CCl$_4$-treated mouse liver.

Ten types of newly expressed growth factor genes were in the CCl$_4$-treated mouse livers (fibroblast growth factor 3 (FGF-3), fibroblast growth factor 5 (FGF-5), fibroblast growth factor 8 (FGF-8), fibroblast growth factor 10 (FGF-10), fibroblast growth factor 13 (FGF-13), fibroblast growth factor 18 (FGF-18), HGF, βNGF, insulin-like growth factor 2 (IGF-2), and transforming growth factor α (TGF α). The expression of five types of growth factor increased from about 1.8 fold to about 5.2 fold in the CCl$_4$-treated livers (FGF4: 2.4 fold, hepatoma-derived growth factor (HDGF): 2.2 fold, insulin-like growth factor 1 (IGF-1): 5.2 fold, mast cell growth factor (MCGF): 2.1 fold, and fibroblast growth factor 1 (FGF-1): 1.8 fold). This data suggests that several growth factors are necessary for liver regeneration.

EXAMPLE 2

Effects of Retinoic Acid (RA)

The present inventers investigated the effects of RA and a single growth factor, LIF, on ES cell differentiation (FIG. 2A). GFP-positive cells were not detected before ES cell differentiation or addition of growth factor. When using medium comprising LIF and RA, a culture period of three days (n=2) was efficient in inducing GFP-positive cells. For example, the proportion of GFP-positive cells in medium comprising HGF, LIF and RA rose from 4.11% to 9.72%. These results, obtained by EGFP expression and alkaline phosphatase staining (data not shown), clearly showed that RA-treated ES cells have retained a number of differential abilities, as pluripotent ES cells. With regards to the effect of RA, ES cells cultured in medium comprising LIF were induced more efficiently than in medium without LIF.

EXAMPLE 3

Effects of Growth Factors on ES Cell Differentiation

The present inventors studied EGFP expression over five days, investigating the effects of growth factors on the induction of ES cell differentiation (FIGS. 2B to 2E). In the absence of medium comprising FGF4, GFP-positive cell formation was inhibited from an early stage when OsM was used alone or in combination with several growth factors. Similarly, aFGF inhibited bFGF-facilitated hepatocyte multiplication, and GFP-positive cells were not detected when FGF4 was combined with any of the bFGF, EGF and/or βNGF mixtures. Induction of GFP-positive cells was detected within three days in medium comprising aFGF, FGF4 and HGF, and the percentage of positive cells was 28.72±5.81% (n=5). In addition, the percentage of GFP-positive cells was also higher in mixed medium comprising activin A and aFGF, mixed medium comprising EGF and aFGF, mixed medium comprising βNGF and aFGF, mixed medium comprising activin A and FGF4, and mixed medium comprising HGF and FGF4; compared to medium comprising each growth factor alone. GFP-positive cells were not detected in control culture dishes, which were not cultured in media comprising growth factors (data not shown).

Previous methods for inducing ES cell differentiation were based on acquiring the ability to differentiate into various cells by first forming EBs and then causing these EBs to differentiate into any of the three germ layer types. However, the results of this Example suggest that pluripotency is not acquired by forming EBs, but it is an ability inherent to ES cells. The rate of differentiation was confirmed to be about four to about eight times greater than that with EB formation (Miyashita, H., Suzuki, A., Fukao, K., Nakauchi, H., and Taniguchi, H., "Evidence for hepatocyte differentiation from embryonic stem cells in vitro.", Cell Transplantation 11: 429-434, 2002).

As described above, it is suggested that by adding the aforementioned growth factors to culture medium, pluripotent ES cells can be induced to differentiate into GFP-positive cells at an efficiency of about one-third, and without forming EBs, which differentiate spontaneously and irregularly. Moreover, it was suggested that differentiation could be directly induced by artificially manipulating ES cells.

EXAMPLE 4

Effects of Matrix on ES Cell Differentiation

Figure 4:
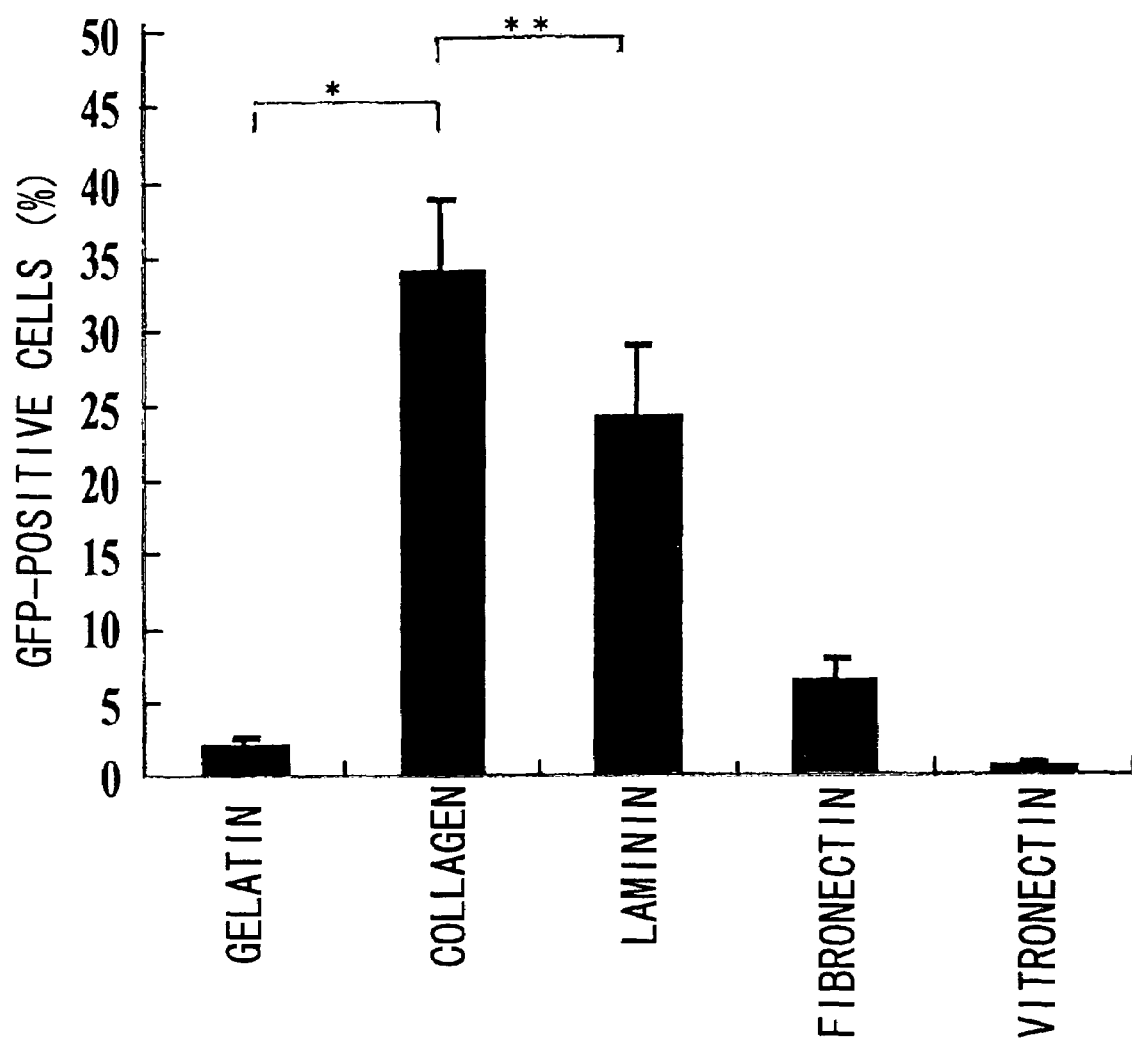
FIG. 4 is a graph showing the percentage of GFP-positive cells on several matrices. Data is represented as the mean±S.D. (*: $P<0.0001$, **: $P<0.01$).

To examine the effect of the culture dish matrix on ES cell differentiation, the present inventors counted the number of GFP-positive cells on five types of matrix-coated culture dish (day 8) (FIGS. 3 and 4). The experiment was carried out by pre-culturing the cells for three days in gelatin-coated culture dishes comprising RA and LIF, then culturing the cells for five days in gelatin-coated culture dishes comprising HGF, aFGF and FGF4, and finally culturing the differentiation-induced cells in each type of coated culture dish comprising OsM. The resulting percentages of GFP-positive cells were as follows: gelatin, 2.26±0.36%; laminin (10 μg/ml), 24.1±4.97%; fibronectin (6 μg/ml) 6.5±1.57%; and vitronectin (1 μg/ml), 0.9±0.47%. GFP-positive cells in the collagen type I-coated culture dishes (n=5) had the greatest percentage of differentiated ES cells, at 38.4% (34.17±4.91%). In the laminin-coated and collagen type I-coated culture dishes, GFP was strongly expressed by OsM in ES cell differentiation. However, the percentage of GFP-positive cells was reduced in dishes with other coatings. Similarly, when collagen type I-coated plates were used in the first stage of culturing, the percentage of GFP-positive cells was reduced, and the growth activity of GFP-negative cells was much greater than the differentiation of GFP-positive cells (data not shown). This data indicates that the matrix plays an important role in ES cell differentiation.

EXAMPLE 5

Analysis of GFP-Positive Cell Type

The GFP-positive cell fractions were investigated using a phase microscope (FIG. 5). GFP-positive cells and differentiated cells were the same. The location of GFP-positive cells was indicated by the production of ALB, a mature hepatocyte marker. However, the results contrasted with hepatocyte type cells.

EXAMPLE 6

Analysis of Liver Gene Expression and Function in GFP-Positive Cell Fractions

To assess the level of liver differentiation, the present inventors investigated the expression of mRNA by liver-specific genes in the GFP-positive cell fractions (FIG. 6A). Mature hepatocyte markers including ALB, TO, TTR, TAT, CK18 and G6P, were positive on day seven of culturing. AFP, a marker specific to immature hepatocytes, was not detected. On the other hand, on day five of culturing, TAT, G6P and CK18 were not detected in GFP-positive cell fractions in a medium comprising HGF, aFGF and FGF4. ALB and TO were detected at low levels, and AFP was not detected. Placebo-treated ES cells did not express these hepatocyte marker genes. These results suggest that GFP-positive cells comprise the characteristics of mature hepatocytes. Mature hepatocytes are finally differentiated hepatocyte cells. Obtaining finally differentiated cells from ES cells is extremely useful in researching and elucidating intermediate differentiation pathways for research on hepatocyte development and differentiation. In addition, the potential for using mature hepatocytes for cell transplant therapy objectives has been confirmed by in vivo experiments using liver disease model mice (Yamamoto, H. et al., Hepatology, 37: 983-993, 2003; and Teratani, T., et al., 2003, submission). Since immature hepatocytes are not fully differentiated, their latent potential for disdifferentiation or abnormal proliferation (e.g., canceration) is thought to be higher than for mature hepatocytes. Thus the acquisition of mature hepatocytes is also advantageous from this point of view.

To further elucidate whether GFP-positive cell fractions comprise hepatocyte-specific function or not, the present inventers performed biochemical analysis (n=2). These results indicated that GFP-positive cell fractions can show glucose-producing ability (FIG. 6B) and also affect the depletion of ammonia from the culture media (FIG. 6C). These results indicate that hepatocytes differentiated from ES cells can grow in vitro over a considerable period of time, whilst retaining hepatocyte characteristics including metabolic activity.

EXAMPLE 7

Treatment of Cirrhosis Model Mice by Transplantation of Hepatocytes Derived from ES Cells Induced by the Present Invention To artificially induce cirrhosis, dimethylnitrosoamine (DMN) was administered intraperitoneally, three times a week for four consecutive weeks, to female mice (age: eight weeks, strain: 129SV). DMN was administered at dosage of 1% in 1 ml of physiological saline per kilogram of mouse body weight. The presence or absence cirrhosis induction was confirmed by the presence of fibrosis, as determined by microscopic examination of liver tissue sections, and by numerical results, obtained by measuring GOT and GPT levels in the serum. GFP-positive cells (hepatocytes derived from mouse ES cells) were prepared using the present differentiation induction system, and $1.0 \times 10^6$ cells per mouse were injected intravenously into the caudal vein four weeks after the final DMN administration. The control group was administered with physiological saline. Each group contained eight mice. Twenty-four hours after transplant, liver sections were observed with a fluorescence microscope, indicating that the hepatocytes, which were GFP-positive cells, were already attaching near cirrhotic lesions in the liver (FIG. 7).

Figure 8:
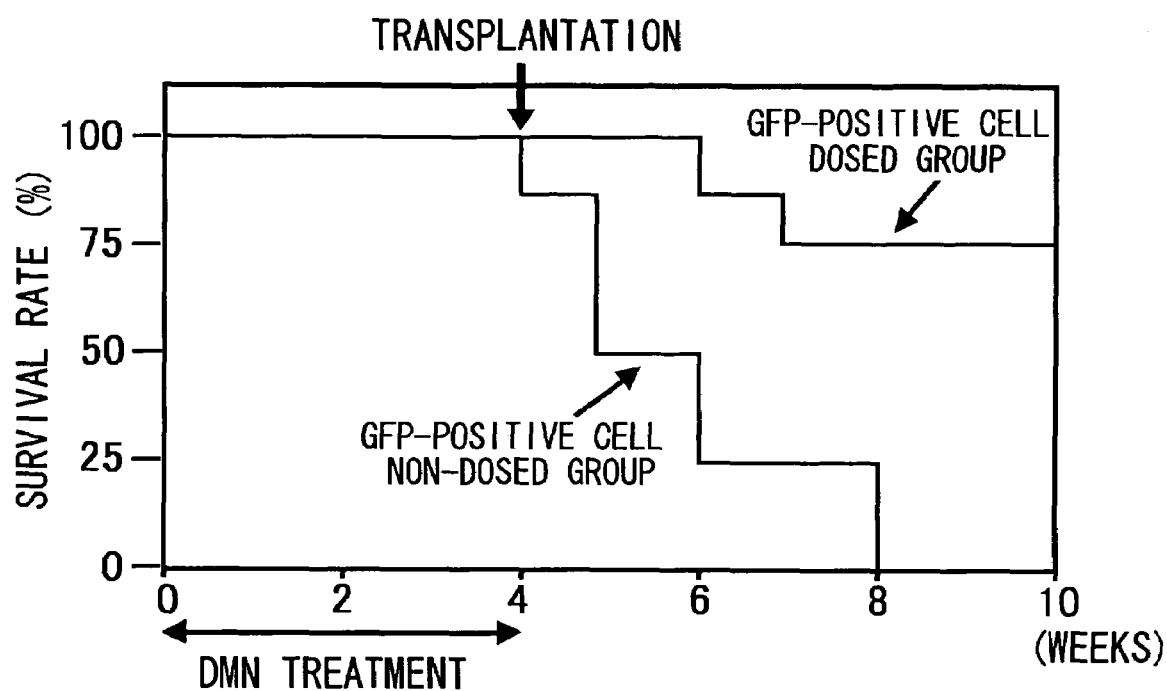
FIG. 8 is a graph comparing survival rates between the GFP-positive cell dosed group and the non-dosed group.

An extremely prominent difference in survival rate was observed on comparing groups that were and were not dosed with GFP-positive cells. Four weeks after DMN administration, all of the non-dosed animals died. In contrast, 75% of animals in the GFP-positive cell dosed group survived, confirming a significant life-prolonging effect in this group (FIG. 8).

Figure 9:
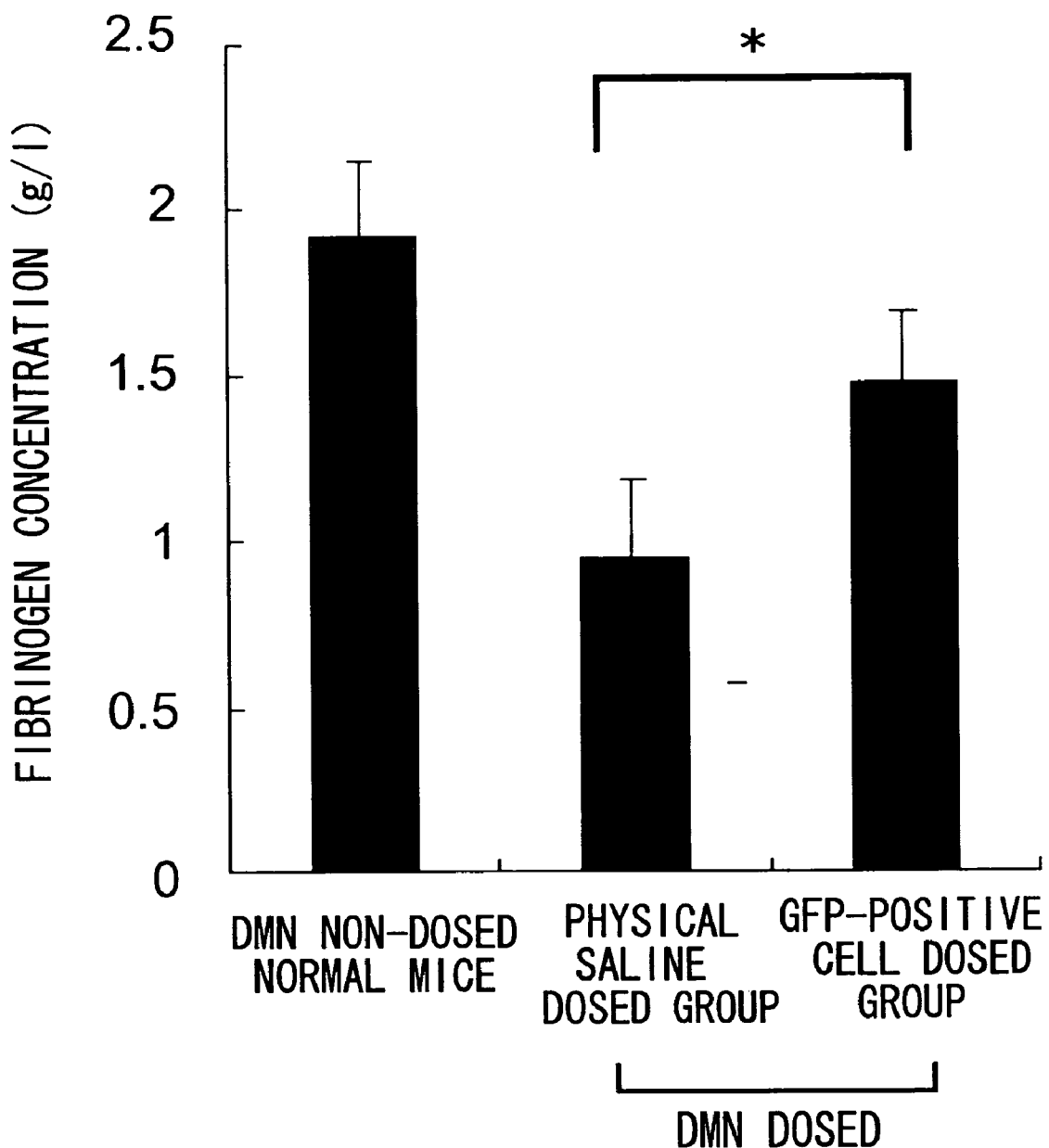
FIG. 9 is a graph showing fluctuations in blood fibrinogen levels (*: $P<0.009$).
Figure 10:
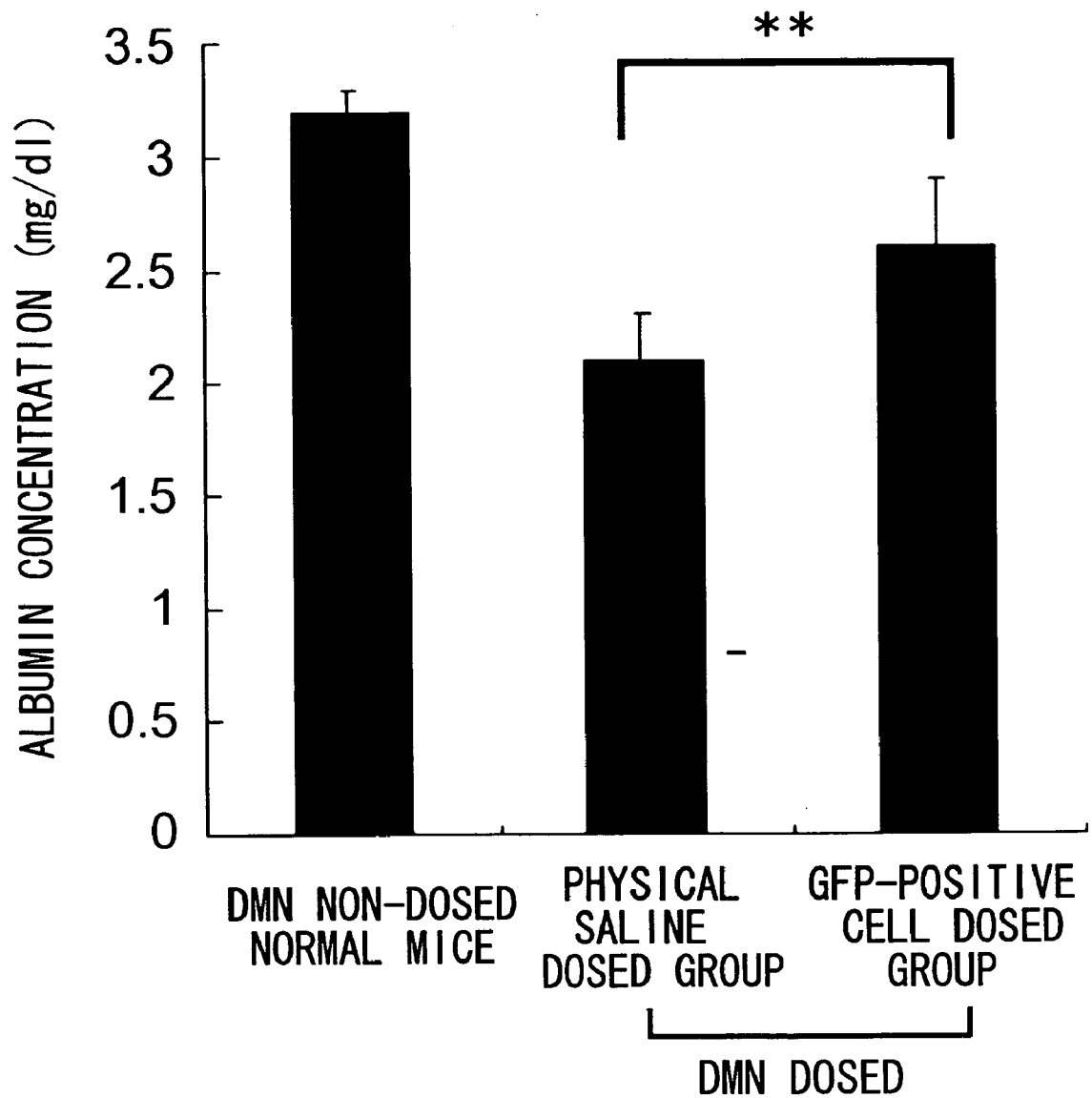
FIG. 10 is a graph showing fluctuations in blood albumin levels (**: $P<0.003$)

When fluctuations in blood level fibrinogen and albumin were investigated, both levels were determined to have recovered to nearly normal two weeks after transplant (FIGS. 9 and 10).

Figure 11:
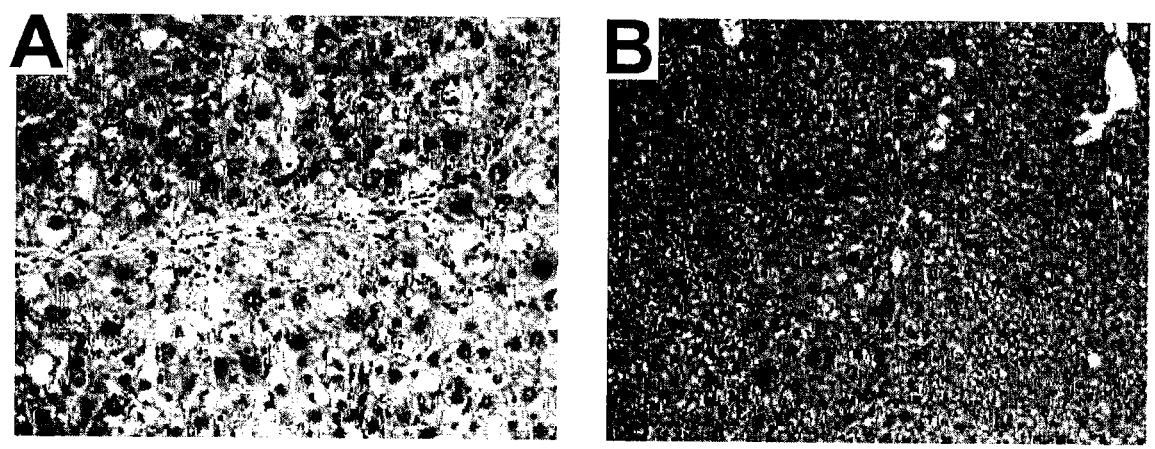
FIG. 11 depicts photographs showing stained tissues obtained from DMN-treated mice. (A) depicts stained liver tissue three weeks after administration of PBS as a control to DMN-treated mice. (B) depicts stained liver tissue three weeks after transplanting GFP-positive hepatocytes into DMN-treated mice.

In addition, three weeks after administering control PBS to DMN-treated mice, prominent cell death and fibrosis was observed in their hepatocytes. However, three weeks after mice similarly treated with DMN were transplanted with GFP-positive hepatocytes, stained hepatocyte tissue samples revealed marked improvements in fibrosis (FIG. 11).

These results suggest that cirrhosis can be treated by transplanting hepatocytes derived from ES cells induced according to the present invention.

EXAMPLE 8

Analysis of the Expression and Function of Liver Genes in Hepatocytes Induced to Differentiate from Cynomolgus Monkey ES Cells Based on findings obtained from mouse ES cells, the present inventors attempted to use primate ES cells from cynomolgus monkeys (CM) to induce differentiation to hepatocytes. The CMES cells were cultured in gelatin-coated culture dishes (Iwaki) in 400 ml of Dulbecco's modified Eagle medium containing 20% fetal calf serum, 5 ml of non-essential amino acids, 5 ml of nucleoside storage solution, 3.5 µl of β-mercaptoethanol, 1000 units/ml of LIF and 50 µg/ml of G418, followed by insertion of pALB-EGFP by electroporation to produce G418-resistant pALB-EGFP/CMES cells. The resulting pALB-EGFP/CMES cells were shown to retain the ability to remain undifferentiated since they possessed alkaline phosphatase activity (FIG. 12A) and the ability to form embryoid bodies (FIG. 12B).

Differentiation to hepatocytes was induced in CMES cells using the present invention's in vitro differentiation induction system, established using mouse ES cells. More specifically, $5.0 \times 10^5$ pALB-EGFP/CMES cells prepared under the aforementioned conditions were cultured at 37° C. for three days in a gelatin-coated culture dish with 1000 units/ml of LIF and $1.0 \times 10^{-8}$ M RA. Pre-cultured ES cells were then inoculated into a gelatin-coated culture dish, followed by the addition of 50 ng/ml of HGF, 20 ng/ml of FGF4 and 100 ng/ml of aFGF. This mixture was then incubated at 37° C. for ten days. Some of the dissociated cells were transferred to a collagen type I-coated dish and cultured at 37° C.

for three days with 10 ng/ml of OsM. 16 days after beginning to induce differentiation, the fraction of GFP-positive cells relative to differentiated cells was investigated. The location of GFP-positive cells was demonstrated by the production of ALB, a mature hepatocyte marker (FIG. 13A). In order to evaluate the level of differentiation to liver cells, mRNA expression by liver-specific genes was investigated in the GFP-positive cell fraction. This investigation showed that mature hepatocyte markers, including ALB, TO, TAT and G6P, were positive (FIG. 13B). These results regarding liver-specific markers, metabolic function and morphology demonstrate that the cells induced to differentiate from CMES cells obtained in this Example were hepatocytes. Thus these results show that hepatocytes can also be produced from primate ES cells.

This Example demonstrates that mouse ES cells can differentiate into hepatocytes with liver-specific functions when pALB-EGFP-transfected ES cells are cultured in DMEM supplemented with HGF, FGF-4, aFGF, and OsM, and the matrix is changed from gelatin to collagen type I (FIG. 1). The most important points in this system are that i) ES cells are cultured in a medium comprising LIF and RA for three days before differentiation, and ii) that efficient differentiation of GFP-positive cells is achieved from ES cells in vitro. Mouse ES cells are thought to have sufficient developmental potential, as they can give rise to derivatives of all three germ layers (mesoderm, ectoderm, and endoderm) in vitro [Evans, M. J. and Kaufman, M. H., Nature 292:154-156, 1981; and Martin, G. R., Proc. Natal. Aced. Sic. USA. 78: 7634-7638, 1981]. According to developmental biology using P19 and F9 embryonic carcinoma cell differentiation systems, these cells are able to differentiate in vitro, and the derivatives of all three embryonic germ layers (mesoderm, ectoderm, and endoderm) can be obtained depending on the culture, AFP synthesis, and retinoic acid (RA) concentration [Sasahara, Y. et al., J. Biol. Chem. 271: 25950-25957, 1996; Grover, A. & Adamson, D. E., Dev. Biol. 114: 492-503, 1986; Hogan, B. L. M. & Tilly, R. J., Embryol. Exp. Morphol. 62: 379-394, 1981; Hogan, B. L. M. et al., Cancer Surveys. 2: 115-140 1983; and Grover, A. et al., J. Cell Biol. 96: 1690-1696, 1983]. Thus, P19 and F9 cells resemble ES cells in that they can induce the three germ layers, even if RA is not added to the culture medium. In this connection, the present inventors demonstrated that the differentiation of GFP-positive cells is determined in effective conditions that use LIF and RA (FIG. 2A). Accordingly, hepatocyte differentiation is efficiently induced when LIF and RA are added to the culture medium. However, even if the ES cells are not pre-cultivated, it is possible to induce hepatocyte differentiation even though the efficiency is low, (FIG. 2A). The ES cells were cultured with the three important growth factors (aFGF, HGF and FGF-4) on gelatin-coated dishes for five days, and further cultured with growth factor (OsM) on collagen type I-coated dishes for two days. This induced ES cell differentiation (FIGS. 2B to 2G, and FIG. 3). aFGF as an FGF-1 is a heparin binding growth factor which stimulates the proliferation of a wide variety of cells, including mesenchymal, neuroectodermal and endothelial cells [Dungan, K. M. et al., J. Exp. Zool. 292: 540-54, 2002]. HGF is a powerful mitogen for mature hepatocytes and biliary epithelial cells [Nakamura, T. et al., Nature. 342: 440-443, 1989; and Jopin, R. et al., J. Clin. Invest. 90: 1284-1289, 1992]. Furthermore, FGF-4 as a heparin binding secretory transforming factor-1 (HST-1) is important in initial endoderm patterning, and may play a role in endoderm determination [Wells, J. M. & Melton, D. A., Development. 127: 1563-1572, 2000]. OsM is an important growth-regulating cytokine that has a variety of effects on a number of tumors and normal cells, and was identified to up-regulate the function of hepatocyte metabolism activation [Sakai, Y. et al., Cell Transplant. 11: 435-441, 2002].

The present inventors used cDNA microarrays to analyze changes in growth factor mRNA expression in $CCl_4$-treated and placebo-treated mouse livers (Table 1). Recent studies suggest that hepatoma-derived growth factor (HDGF) is highly expressed in developing liver, and promotes fetal hepatocyte proliferation in mice; and that insulin-like growth factors-I and -II (IGF-I and II) induce the differentiation of hepatocytes in rats [Enomoto, H. et al., Hepatology. 36: 1519-1527, 2002; and Streck, R. D. & Pintar, J. E., Endocrinology. 131: 2030-2032, 1992]. HGF and transforming growth factor α (TGF α) relate to various stages of hepatocyte proliferation [Fausto, N. J. Hepatol. 32: 19-31, 2000; and Michalopoulos, G. K. & DeFrances, M. C., Science. 276: 60-66, 1997]. The present inventors had earlier detected HGF expression in the regeneration of mouse liver using Western blotting analysis. Accordingly, the cDNA microarray data was reliable. However, the present inventors found that differentiation of hepatocytes from ES cells is related to the matrix (FIG. 4). Usually, collagen-coated and laminin-coated dishes are used for hepatocyte cultivation. Thus, efficient differentiation of functional hepatocytes from ES cells was possible without EB formation. To understand this mechanism in more detail, hepatic regeneration such as growth factor expression in a number of hepatic diseases was essential [Fausto, N. J., Hepatol. 32: 19-31, 2000; and Hoffman, A. L. et al., Seminars Liv. Dis. 14: 190-210, 1994].

Previous reports have suggested that endoderm-specific gene expression was derived from the EB visceral endoderm [Abe, K. et al., Exp. Cell Res. 229: 27-34, 1996]. However, in the Examples, the expression of mature hepatocyte markers was detected. For example, TTR is expressed during liver maturation and represents endodermal or yolk-sac-like differentiation [Makover A, et al., Differentiation. 40:17-25, 1989]. Expression of ALB, the most abundant protein synthesized by mature hepatocytes, begins in early fetal hepatocytes (E12), and peaks in adult hepatocytes [Sellem, C. H. et al., Dev. Biol. 102: 51-60, 1984]. TAT is an excellent enzymatic marker for peri- or postnatal hepatocyte-specific differentiation. This enzyme is not synthesized in significant quantities prior to birth, but is rapidly activated early in the neonatal developmental period [Greengard, O., Science. 163:891-895, 1969]. G6P expression has been observed in the liver from the perinatal period, and its proteins play a role in gluconeogenesis [Burcelin, R. et al., J. Biol. Chem. 275: 10930-10936, 2000]. In recent reports, EBs were differentiated into hepatocytes by plating on gelatin-coated dishes, and incubating for several days without LIF and growth factors [Hamazaki, T., Iiboshi, Y., and Oka, M. et al., FEBS Lett. 497: 15-19, 2001; and Miyashita, H. et al., Cell Transplantation. 11: 429-434, 2002]. Similarly, the present inventors used RT-PCR to detect hepatic genes in the GFP-positive cell fraction which was differentiated as hepatocytes (FIG. 6A). Moreover, on investigating the in vitro metabolic activity of the GFP-positive cell fractions, the present inventers found that ES-derived hepatocytes expressed liver functions (FIGS. 6B and 6C). These findings suggest that the differentiation of functional mature hepatocytes from ES cells does not require EB formation, and differentiation is possible in a shorter time than in general methods which use EB formation.

The present inventers have previously demonstrated that ES cells can differentiate into hepatic cells if transplanted and established in liver-damaged mouse recipients. Using this method, ES cells could be efficiently induced to differentiate into functional hepatocytes in 14% to 28% of the teratomas generated in this system [Yamamoto, H. et al., Hepatology. 37: 983-993, 2003]. Although hepatocyte production can be achieved by in vitro systems, it was possible that the produced cells were fusion cells between the original hepatocytes and the ES cells. However, the present inventors have presented data that clearly demonstrates, for the first time, that functional hepatocytes can be directly induced from ES cells in vitro, and that the GFP-positive cells are not fusion products between normal hepatocytes and ES cells.

The present invention demonstrates that the in vitro ES cell differentiation system is a useful model for analyzing the role of specific growth factors and intracellular signaling molecules in hepatic development, and may be the basis for stem cell therapies applicable in treating hepatic diseases.

EXAMPLE 9

Establishment of pALB-EGFP/hMSCs

Figure 14:
FIG. 14 is a photograph showing the characteristics of human mesenchymal stem cells used in the present invention. Object lens×20.

Human marrow cell-derived normal mesenchymal stem cells (hMSCs) (FIG. 14) were purchased from Sanko Junyaku Co., Ltd. (Tokyo, Japan). The cells were cultured using a mesenchymal stem cell medium kit (Takara Co., Ltd., Kyoto, Japan) and non-coated culture dishes (Iwaki Co., Ltd., Tokyo, Japan). A system enabling the simple detection, using a fluorescence microscope, of induced hMSC differentiation to hepatocytes was required. To this end, a vector in which an EGFP sequence was bound downstream of a human albumin promoter sequence (Quinn G., et al., BBRC, 276: 1089-1099, 2000) was introduced to genes using electroporation. The electroporation conditions adopted were those for cynomolgus monkey ES cells (concentration of the gene to be introduced: 50 μg, 420 V, 25 μF, $1.0 \times 10^7$ cells/0.4 ml opti MEM). Meanwhile, the neomycin (G418; Gibco BRL, Funakoshi Co., Ltd., Tokyo, Japan) sensitivity of hMSCs in which genes had not been introduced was studied in order to select drugs, and a concentration of neomycin was decieded upon (FIG. 15). This neomycin concentration was thereafter used to maintain and induce pALB/hMSC differentiation.

EXAMPLE 10

Differentiation Induction

Figure 16:
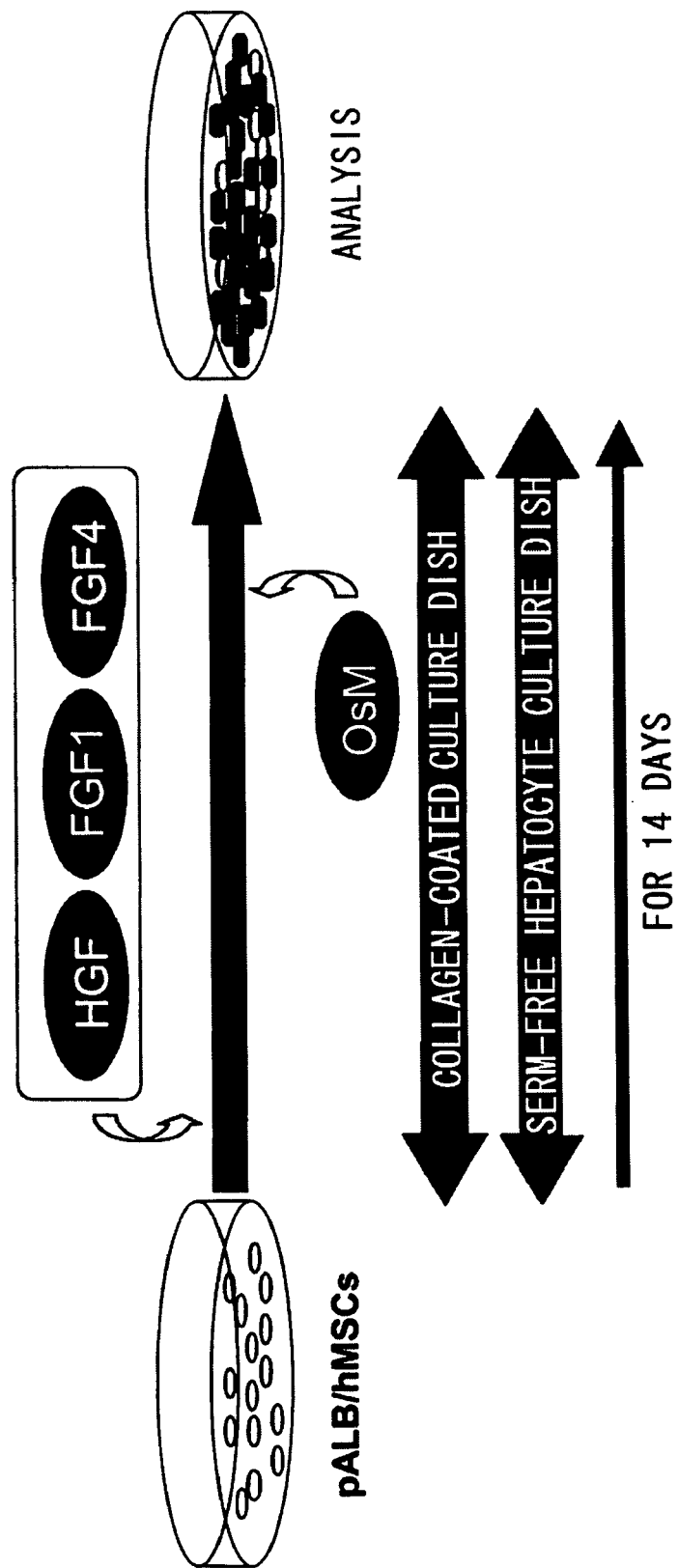
FIG. 16 is a figure showing the induction of in vitro pALB/hMSC differentiation.

After gene introduction, drug selection was carried out using neomycin, and cloned human MSCs were obtained (hereinafter referred to as pALB/hMSCs). The differentiation of pALB/hMSCs into hepatocytes was initiated using the HIFC differentiation induction system established in ES cells. Each cell growth factor was added to the culture medium in concentrations adopted from cynomolgus monkey ES cells (HGF: 200 ng/ml, aFGF: 300 ng/ml, FGF4: 60 ng/ml; Veritas Corporation, Tokyo, Japan). Differentiation was induced for ten days using a collagen-coated culture dish (Iwaki Co., Ltd., Tokyo, Japan) and serum-free hepatocyte culture medium (HMC; Sanko Junyaku Co., Ltd., Tokyo, Japan) comprising growth factors. Oncostatin M (Veritas Corporation, Tokyo, Japan) was then added to the culture solution (HMC) at a concentration of 10 ng/ml, and further culturing was performed for a four day maturing term (FIG. 16). On day 14, GFP-positive cells, indicating the acquisition of albumin producing ability, were detected under a fluorescent microscope (FIG. 17).

EXAMPLE 11

Characteristics of GFP Positive pALB/hMSCs

Figure 18:
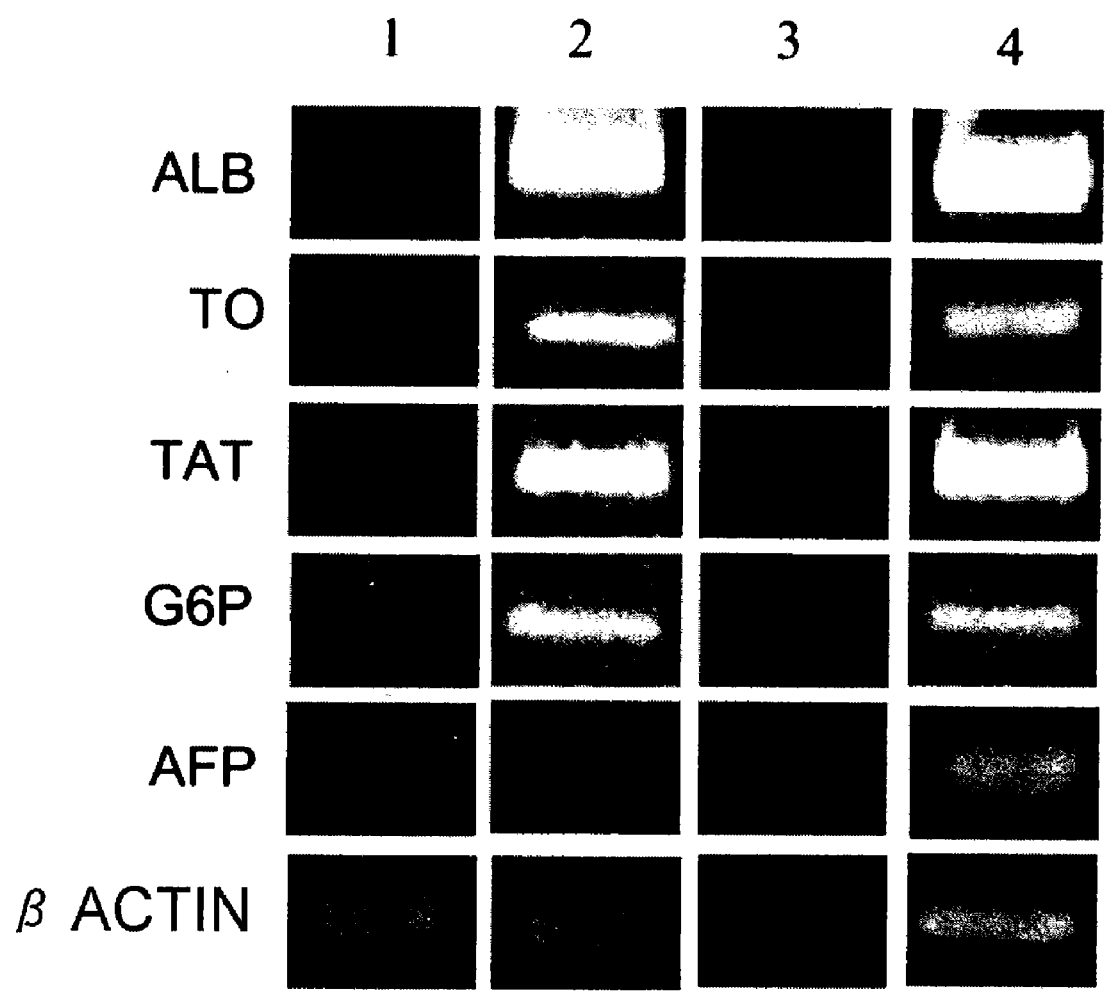
FIG. 18 is photographs showing the results of expression of hepatocyte-specific marker genes of pALB/hMSCs cultured and differentiated in vitro. Lane 1: cDNA of untreated pALB/hMSCs; lane 2: cDNA of the differentiated pALB/hMSC fraction (day 14); lane 3: genomic DNA of untreated pALB/hMSCs; and lane 4: the positive control (ALB, TO, TAT and G6P are cDNAs derived from normal human cultured hepatocytes (Sanko Junyaku Co., Ltd., Tokyo, Japan), and AFP is that derived from HepG2). ALB, TO, TAT and G6P were all four positive 14 days after the initiation of differentiation induction. However, amplified AFG gene fragments, which indicate immature hepatocytes, were not detected during the 14 days of differentiation induction.

Total RNA was extracted using ISOGEN (Nippon Gene Co., Ltd., Tokyo, Japan). A single-stranded cDNA was synthesized in a total volume of 20 μl of a solution containing 2 μg of the total RNA, 0.5 μl of an oligo(dT)$_{18}$ primer, 10 pmol of dNTP, 5 units of RAV-2 RTase, and a single-stranded chain synthesizing buffer (Takara Co., Ltd., Kyoto, Japan). Synthesis was performed at 36° C. for ten minutes, at 42° C. for one hour, at 56° C. for ten minutes, and at 99° C. for five minutes. In addition, the following primers were synthesized (oligonucleotide information is in the following order: sense primer; antisense primer; annealing temperature; PCR cycles; amplified fragment length): albumin (ALB) (5-GCAACACAAAGATGACAACCN-3 (SEQ ID No: 17); 5-TCCTTGGCCTCAGCATAGTTN-3 (SEQ ID No: 18); 60° C.; 32 cycles; 665 bp), tryptophan 2,3-dioxygenase(TO) (5-CTGAAGAAAAAGAGGAACAGN-3 (SEQ ID No: 19); 5-TCTGTGCACCATGCACACATN-3 (SEQ ID No: 20); 58° C.; 34 cycles; 265 bp), tyrosine aminotransferase (TAT) (5-CTGGTGAAGCTGAGT-CAGCGN-3 (SEQ ID No: 21); 5-TCACAGAACTCCTG-GATCCGN-3 (SEQ ID No: 22); 58° C.; 34 cycles; 394 bp), glucose-6-phosphatase (G6P) (5-TTGTGGTTGGGAT-TCTGGGCN-3 (SEQ ID No: 23); 5-GCTGGCAAAGGGT-GTAGTGTN-3 (SEQ ID No: 24); 55° C.; 42 cycles; 320 bp), α-fetoprotein (AFP) (5-TCGTATTCCAACAG-GAGG-3 (SEQ ID No: 25); 5-AGGCTTTTGCTTCAC-CAG-3 (SEQ ID No: 26); 54° C.; 42 cycles; 173 bp), β actin (5-AGAGCAAGAGAGGTATCCTG-3 (SEQ ID No: 27); 5-AGAGCATAGCCCTCGTAGAT-3 (SEQ ID No: 28); 55° C.; 25 cycles; 339 bp). Amplification was performed in a total volume of 50 μl containing 4 μl of a template cDNA, 100 μM dNTPs, 10 pmol of a primer, 1.0 unit of Ex-Taq and an Ex-Taq buffer (Takara Co., Ltd., Kyoto, Japan). After PCR, aliquots were run on 3.0% agarose gels, stained with ethidium bromide (EtBr), and then photographed under UV irradiation (FIG. 18). Furthermore, chromosomes of the GFP positive pALB/hMSCs (day 14 after differentiation induction) were analyzed using a G-band method (FIG. 19).

The present differentiation inducing system is a system in which stimulation of cell growth factors is used to induce differentiation in a near natural state. Results gained by using the system revealed that the CD34 negative fraction also comprises the ability of differentiating into hepatocytes. Furthermore, a combination of cell growth factors developed (discovered) by the present inventors was confirmed for the first time to be applicable not only to ES cells but also to marrow cell-derived mesenchymal stem cells.

The invention claimed is:

1. A method for inducing differentiation of mesenchymal stem cells to hepatocytes comprising
    (a) culturing the mesenchymal stem cells in a medium comprising acidic fibroblast growth factor, fibroblast growth factor 4, and hepatocyte growth factor; and then
    (b) culturing the cells cultured in step (a) in a medium comprising oncostatin M, thereby differentiating the mesenchymal stem cells into hepatocytes.

2. The method according to claim 1, wherein the cells are cultured on a gelatin-coated culture dish in step (a), and the cells are cultured on a collagen type I-coated culture dish or laminin-coated culture dish in step (b).

3. The method according to claim 1, wherein the cells are cultured on a gelatin-coated culture dish.

4. A method according to claim 1, wherein the mesenchymal stem cells are derived from a mamnnal.

5. The method according to claim 3, wherein the mammal is a human, monkey, mouse, rat or pig.

6. A method for inducing differentiation of embryonic stem cells to hepatocytes comprising
    (a) culturing the embryonic stem cells in a medium comprising retinoic acid, leukemia inhibitory factor, and hepatocyte growth factor; and then
    (b) culturing the cells cultured in step (a) in a medium comprising acidic fibroblast growth factor, fibroblast growth factor 4, and hepatocyte growth factor; and then
    (c) culturing the cells cultured in step (b) in a medium comprising oncostatin M, thereby differentiating the embryonic stem cells into hepatocytes.

7. The method according to claim 6, wherein the cells are cultured on a gelatin-coated culture dish in steps (a) and (b), and the cells are cultured on a collagen I-coated culture dish or laminin-coated culture dish in step (c).

8. The method of claim 1 or 6 wherein the hepatocytes are mature hepatocytes.

* * * * *

UNITED STATES PATENT AND TRADEMARK OFFICE
CERTIFICATE OF CORRECTION

| | | |
|---|---|---|
| PATENT NO. | : 7,332,336 B2 | Page 1 of 1 |
| APPLICATION NO. | : 10/789159 | |
| DATED | : February 19, 2008 | |
| INVENTOR(S) | : Ochiya et al. | |

It is certified that error appears in the above-identified patent and that said Letters Patent is hereby corrected as shown below:

Column 30, Claim 7: After "collagen" replace "I-coated" with --type I-coated--.

Signed and Sealed this

Fifteenth Day of July, 2008

JON W. DUDAS
*Director of the United States Patent and Trademark Office*

UNITED STATES PATENT AND TRADEMARK OFFICE
CERTIFICATE OF CORRECTION

PATENT NO.         : 7,332,336 B2  
APPLICATION NO. : 10/789159  
DATED                 : February 19, 2008  
INVENTOR(S)       : Ochiya et al.

Page 1 of 1

It is certified that error appears in the above-identified patent and that said Letters Patent is hereby corrected as shown below:

Column 30, Claim 7, line 55: After "collagen" replace "I-coated" with --type I-coated--.

This certificate supersedes the Certificate of Correction issued July 15, 2008.

Signed and Sealed this

Fifth Day of August, 2008

JON W. DUDAS  
*Director of the United States Patent and Trademark Office*

UNITED STATES PATENT AND TRADEMARK OFFICE
CERTIFICATE OF CORRECTION

| | |
|---|---|
| PATENT NO. | : 7,332,336 B2 |
| APPLICATION NO. | : 10/789159 |
| DATED | : February 19, 2008 |
| INVENTOR(S) | : Ochiya et al. |

Page 1 of 1

It is certified that error appears in the above-identified patent and that said Letters Patent is hereby corrected as shown below:

Column 29, Claim 5: After "claim" replace "3" with --4--.

Signed and Sealed this

Nineteenth Day of January, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,332,336 B2 | Page 1 of 1 |
| APPLICATION NO. | : 10/789159 | |
| DATED | : February 19, 2008 | |
| INVENTOR(S) | : Ochiya et al. | |

It is certified that error appears in the above-identified patent and that said Letters Patent is hereby corrected as shown below:

Column 29, Claim 5, lines 59-60: After "claim" replace "3" with --4--.

This certificate supersedes the Certificate of Correction issued January 19, 2010.

Signed and Sealed this

Ninth Day of February, 2010

David J. Kappos
*Director of the United States Patent and Trademark Office*

SEQUENCE LISTING

<160> NUMBER OF SEQ ID NOS: 28

<210> SEQ ID NO 1
<211> LENGTH: 18
<212> TYPE: DNA
<213> ORGANISM: Artificial
<220> FEATURE:

-continued

```
<223> OTHER INFORMATION: An artificially synthesized primer sequence

<400> SEQUENCE: 1
gctacggcac agtgcttg                                                 18

<210> SEQ ID NO 2
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 2
caggattgca gacagatagt c                                             21

<210> SEQ ID NO 3
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 3
tgcgcaagaa cttcagagtg a                                             21

<210> SEQ ID NO 4
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 4
agcaacagct cattgtagtc t                                             21

<210> SEQ ID NO 5
<211> LENGTH: 18
<212> TYPE: DNA
<213> ORGANISM: Artificial
<220> FEATURE:
<223> OTHER INFORMATION: An artificially synthesized primer sequence

<400> SEQUENCE: 5
ctcaccacag atgagaag                                                 18

<210> SEQ ID NO 6
<211> LENGTH: 18
<212> TYPE: DNA
<213> ORGANISM: Artificial
<220> FEATURE:
<223> OTHER INFORMATION: An artificially synthesized primer sequence

<400> SEQUENCE: 6
ggctgagtct ctcaattc                                                 18

<210> SEQ ID NO 7
<211> LENGTH: 18
<212> TYPE: DNA
<213> ORGANISM: Artificial
<220> FEATURE:
<223> OTHER INFORMATION: An artificially synthesized primer sequence

<400> SEQUENCE: 7
accttcaatc ccatccga                                                 18
```

```
<210> SEQ ID NO 8
<211> LENGTH: 18
<212> TYPE: DNA
<213> ORGANISM: Artificial
<220> FEATURE:
<223> OTHER INFORMATION: An artificially synthesized primer sequence

<400> SEQUENCE: 8
tcccgactgg ataggtag                                                 18

<210> SEQ ID NO 9
<211> LENGTH: 18
<212> TYPE: DNA
<213> ORGANISM: Artificial
<220> FEATURE:
<223> OTHER INFORMATION: An artificially synthesized primer sequence

<400> SEQUENCE: 9
tcgtattcca acaggagg                                                 18

<210> SEQ ID NO 10
<211> LENGTH: 18
<212> TYPE: DNA
<213> ORGANISM: Artificial
<220> FEATURE:
<223> OTHER INFORMATION: An artificially synthesized primer sequence

<400> SEQUENCE: 10
aggcttttgc ttcaccag                                                 18

<210> SEQ ID NO 11
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 11
tgattgctga cctgaggaac                                               20

<210> SEQ ID NO 12
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 12
caaacaccgg aatccatacg                                               20

<210> SEQ ID NO 13
<211> LENGTH: 22
<212> TYPE: DNA
<213> ORGANISM: Artificial
<220> FEATURE:
<223> OTHER INFORMATION: An artificially synthesized primer sequence

<400> SEQUENCE: 13
tggtactctc ctcaatctgc tg                                            22

<210> SEQ ID NO 14
<211> LENGTH: 22
<212> TYPE: DNA
<213> ORGANISM: Artificial
<220> FEATURE:
<223> OTHER INFORMATION: An artificially synthesized primer sequence
```

-continued

```
<400> SEQUENCE: 14
ctctggattg actgtggaag tg                                              22

<210> SEQ ID NO 15
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 15
agagcaagag aggtatcctg                                                 20

<210> SEQ ID NO 16
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 16
agagcatagc cctcgtagat                                                 20

<210> SEQ ID NO 17
<211> LENGTH: 21
<212> TYPE: DNA
<213> ORGANISM: Artificial
<220> FEATURE:
<223> OTHER INFORMATION: An artificially synthesized primer sequence
<220> FEATURE:
<221> NAME/KEY: misc_feature
<222> LOCATION: (21)..(21)
<223> OTHER INFORMATION: "n" indicates a, t, g, or c.

<400> SEQUENCE: 17
gcaacacaaa gatgacaacc n                                               21

<210> SEQ ID NO 18
<211> LENGTH: 21
<212> TYPE: DNA
<213> ORGANISM: Artificial
<220> FEATURE:
<223> OTHER INFORMATION: An artificially synthesized primer sequence
<220> FEATURE:
<221> NAME/KEY: misc_feature
<222> LOCATION: (21)..(21)
<223> OTHER INFORMATION: "n" indicates a, t, g, or c.

<400> SEQUENCE: 18
tccttggcct cagcatagtt n                                               21

<210> SEQ ID NO 19
<211> LENGTH: 21
<212> TYPE: DNA
<213> ORGANISM: Artificial
<220> FEATURE:
<223> OTHER INFORMATION: An artificially synthesized primer sequence
<220> FEATURE:
<221> NAME/KEY: misc_feature
<222> LOCATION: (21)..(21)
<223> OTHER INFORMATION: "n" indicates a, t, g, or c.

<400> SEQUENCE: 19
ctgaagaaaa agaggaacag n                                               21

<210> SEQ ID NO 20
<211> LENGTH: 21
```

```
<212> TYPE: DNA
<213> ORGANISM: Artificial
<220> FEATURE:
<223> OTHER INFORMATION: An artificially synthesized primer sequence
<220> FEATURE:
<221> NAME/KEY: misc_feature
<222> LOCATION: (21)..(21)
<223> OTHER INFORMATION: "n" indicates a, t, g, or c.

<400> SEQUENCE: 20
tctgtgcacc atgcacacat n                                              21

<210> SEQ ID NO 21
<211> LENGTH: 21
<212> TYPE: DNA
<213> ORGANISM: Artificial
<220> FEATURE:
<223> OTHER INFORMATION: An artificially synthesized primer sequence
<220> FEATURE:
<221> NAME/KEY: misc_feature
<222> LOCATION: (21)..(21)
<223> OTHER INFORMATION: "n" indicates a, t, g, or c.

<400> SEQUENCE: 21
ctggtgaagc tgagtcagcg n                                              21

<210> SEQ ID NO 22
<211> LENGTH: 21
<212> TYPE: DNA
<213> ORGANISM: Artificial
<220> FEATURE:
<223> OTHER INFORMATION: An artificially synthesized primer sequence
<220> FEATURE:
<221> NAME/KEY: misc_feature
<222> LOCATION: (21)..(21)
<223> OTHER INFORMATION: "n" indicates a, t, g, or c.

<400> SEQUENCE: 22
tcacagaact cctggatccg n                                              21

<210> SEQ ID NO 23
<211> LENGTH: 21
<212> TYPE: DNA
<213> ORGANISM: Artificial
<220> FEATURE:
<223> OTHER INFORMATION: An artificially synthesized primer sequence
<220> FEATURE:
<221> NAME/KEY: misc_feature
<222> LOCATION: (21)..(21)
<223> OTHER INFORMATION: "n" indicates a, t, g, or c.

<400> SEQUENCE: 23
ttgtggttgg gattctgggc n                                              21

<210> SEQ ID NO 24
<211> LENGTH: 21
<212> TYPE: DNA
<213> ORGANISM: Artificial
<220> FEATURE:
<223> OTHER INFORMATION: An artificially synthesized primer sequence
<220> FEATURE:
<221> NAME/KEY: misc_feature
<222> LOCATION: (21)..(21)
<223> OTHER INFORMATION: "n" indicates a, t, g, or c.

<400> SEQUENCE: 24
gctggcaaag ggtgtagtgt n                                              21

<210> SEQ ID NO 25
```

```
<211> LENGTH: 18
<212> TYPE: DNA
<213> ORGANISM: Artificial
<220> FEATURE:
<223> OTHER INFORMATION: An artificially synthesized primer sequence

<400> SEQUENCE: 25
tcgtattcca acaggagg                                                 18

<210> SEQ ID NO 26
<211> LENGTH: 18
<212> TYPE: DNA
<213> ORGANISM: Artificial
<220> FEATURE:
<223> OTHER INFORMATION: An artificially synthesized primer sequence

<400> SEQUENCE: 26
aggcttttgc ttcaccag                                                 18

<210> SEQ ID NO 27
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 27
agagcaagag aggtatcctg                                               20

<210> SEQ ID NO 28
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 28
agagcatagc cctcgtagat                                               20
```